United States Patent [19]
Hudson et al.

[11] Patent Number: 5,861,946
[45] Date of Patent: Jan. 19, 1999

[54] SYSTEM FOR PERFORMING CONTACT ANGLE MEASUREMENTS OF A SUBSTRATE

[75] Inventors: David M. Hudson, Chelmsford; Richard A. Loder, Tyngsboro; Wen-Chu Tseng, Westford; Yueh-Ju Lee, Lowell, all of Mass.

[73] Assignee: AST, Inc., Billerica, Mass.

[21] Appl. No.: 811,691

[22] Filed: Mar. 4, 1997

[51] Int. Cl.$^6$ .............. G01B 1/00; G01B 11/26; G01N 13/02
[52] U.S. Cl. .............. 356/150; 356/138; 356/154; 356/399; 356/375
[58] Field of Search .............. 356/138, 150, 356/154, 399, 375

[56] References Cited

U.S. PATENT DOCUMENTS

| 4,050,822 | 9/1977 | Grat . | |
|---|---|---|---|
| 4,688,938 | 8/1987 | Demoulin et al. | 356/154 |
| 5,137,352 | 8/1992 | Blitshteyn et al. | 356/138 |
| 5,268,733 | 12/1993 | Wright et al. | 356/150 |
| 5,552,341 | 9/1996 | Lee | 437/192 |

*Primary Examiner*—Frank G. Font
*Assistant Examiner*—Jason D. Vierra-Eisenberg
*Attorney, Agent, or Firm*—Fish & Richardson P.C.

[57] ABSTRACT

A system is provided for positioning a substrate having a surface required to be characterized with a contact angle measurement. The system includes a stage which supports the substrate and a dispenser assembly having a dispensing tip through which a liquid droplet having a preselected volume is dispensed onto the surface of the substrate. A first actuating mechanism moves the stage in response to first actuation signals and a second actuating mechanism which changes the vertical spacing between the dispensing tip and the surface of the substrate and dispenses the liquid droplet from the dispenser assembly in response to second actuation signals. A controller is connected to the actuating mechanisms and delivers the first and second actuation signals to the first and second actuating mechanisms, respectively, so as to place the liquid droplet at a predetermined location on the surface of the substrate for performing the contact angle measurement.

5 Claims, 7 Drawing Sheets

SYSTEM FOR PERFORMING CONTACT ANGLE MEASUREMENTS OF A SUBSTRATE

BACKGROUND OF THE INVENTION

This invention relates to a surface analysis system.

In general, a surface analysis system is an instrument which provides a quantitative assessment of the properties of a surface, for example, of a semiconductor wafer.

One technique for assessing the quality of the surface of a semiconductor wafer is by performing a contact angle measurement. A contact angle measurement is a simplified method of characterizing the interfacial tension present between a solid, a liquid, and a vapor. The contact angle is defined as the angle between the support surface and the tangent to the profile of the droplet at the point of contact of the liquid droplet with the surface.

The value of the contact angle of the liquid droplet will depend upon surface wettability. If perfect or complete wetting takes place between the liquid and the surface, the solid surface energy exceeds the liquid surface tension, the droplet spreads out over the surface, and the contact angle approaches zero degree. Thus, the droplet has a flatter, lower profile shape, for example, in the case when wine wets or "sheets" the surface of a glass. On the other hand, when a droplet of a high surface tension liquid rests on a solid of low energy, wetting is only partial, and the resulting contact angle will lie in the range of 0 to 180 degrees. In this case, the liquid surface tension will cause the droplet to form a spherical shape (the lowest energy shape); one example is the way water droplets "bead up" on the surface of a freshly waxed car. A detailed description of contact angle measurements is found in "Contact Angle, Wettability and Adhesion", edited by K. L. Mittal, VSP BV, The Netherlands, 1993, which is incorporated herein by reference.

Contact angle measurements can be used to determine surface cleanliness, primer efficacy, coating uniformity, and oxide thickness. One application in which measuring the contact angle is particularly useful is in evaluating the quality of hexamethyldisilazane (HMDS) deposited on a semiconductor wafer surface. HMDS is typically deposited over portions of a wafer prior to depositing a layer of photoresist which serves as a mask in a subsequent etching process and is then removed. Depositing HMDS is recognized as a critical surface preparation step to ensure that the photoresist adheres properly to substrate so that "under etching" is minimized.

Devices are known for determining the contact angle of a droplet, both by direct measurement of the angle and by indirect calculation based upon measurement of the height, width, or radius of the droplet. One common technique involves projecting a silhouette image of the deposited droplet on a projection screen and determining the contact angle by direct or indirect measurements taken from the silhouette.

SUMMARY OF THE INVENTION

This invention provides a system for accurately and reproducibly implementing contact angle measurements. In particular, the system allows a liquid droplet to be deposited onto a precise location of a substrate (e.g., semiconductor wafer) having a surface whose surface energy is required to be characterized. Unlike prior schemes, in which the operator must subjectively observe the droplet (e.g., with a microscope) to determine the contact angle, the system uses automatic image analysis to eliminate observation errors caused by operator subjectivity (e.g., parallax). The manner in which the wafers are positioned and analyzed minimizes operator intervention, thereby reducing the risk of damage caused by handling.

In a general aspect of the invention, the system includes a stage which supports the substrate; a dispenser assembly having a dispensing tip through which a liquid droplet having a preselected volume is dispensed onto the surface of the substrate; a first actuating mechanism which moves the stage in response to first actuation signals; a second actuating mechanism which changes the vertical spacing between the dispensing tip and the surface of the substrate and dispenses the liquid droplet from the dispenser assembly in response to second actuation signals; and a controller connected to the actuating mechanisms to deliver the first and second actuation signals to the first and second actuating mechanisms, respectively, so as to place the liquid droplet at a predetermined location of the surface of the substrate for performing the contact angle measurement.

Embodiments of the invention may include one or more of the following features. The first actuating mechanism includes a first actuator which moves the stage in a horizontal direction, and a second actuator which rotates the stage. The controller includes a first motor controller unit and a second motor controller unit which together provide the first actuation signals to the first and second actuators, respectively.

The second actuating mechanism includes a third actuator which changes the vertical spacing between the dispensing tip and the surface of the substrate, and a fourth actuator which dispenses the liquid droplet from the dispenser assembly. The controller includes a third motor controller unit and a fourth motor controller unit which together provide the second actuation signals to the third and fourth actuators, respectively.

The dispenser assembly includes a syringe for carrying liquid, the syringe having a first end connected to the dispensing tip and a second end having a plunger connected to the fourth actuator. The stage includes stop members which contact an edge of the substrate and the dispenser assembly includes a paddle member which is used to move the substrate into contact with the stop members, so that the substrate is substantially centered on the stage. The first actuating mechanism includes a lead screw and a belt and capstan mechanism which both connect the first and second actuator, respectively, to the stage.

DETAILED DESCRIPTION

Figure 1:
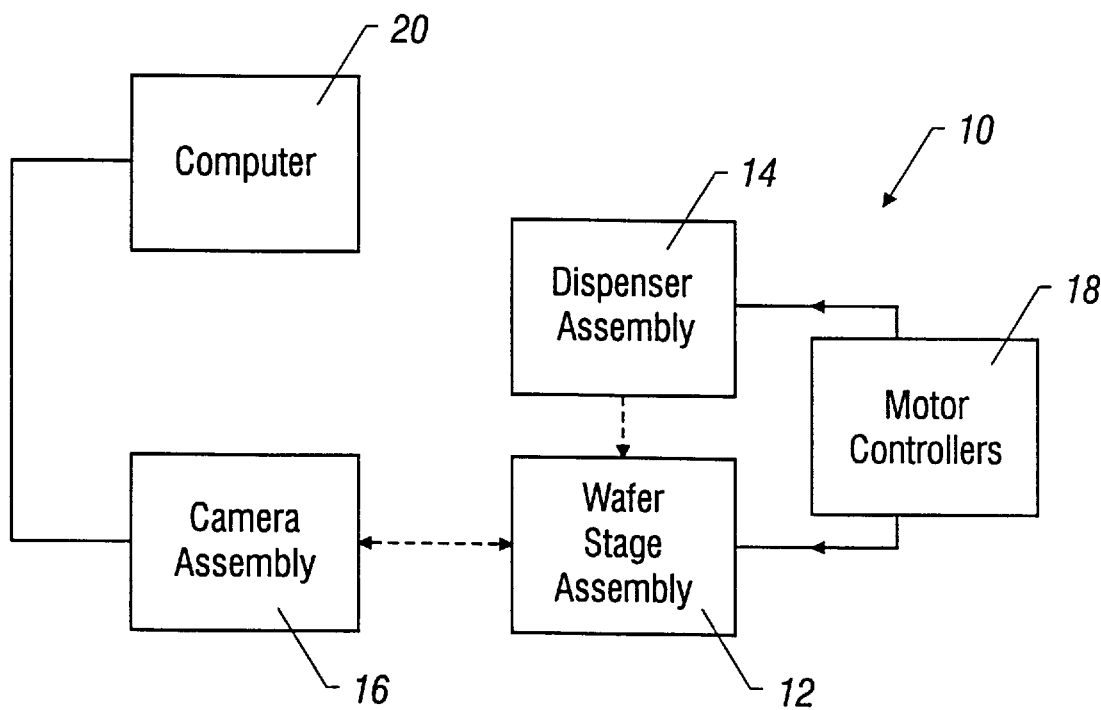
FIG. 1 is a block diagram of the surface analysis system.

Referring to FIG. 1, a wafer surface analysis system 10, for example, a VCA 3000 series machine available from AST Products, Billerica, Mass., includes a wafer stage assembly 12, a dispenser assembly 14, and a video camera assembly 16, each of which will be described in greater detail below. Wafer surface analysis system 10 also includes a motor controller 18 which controls the movement of wafer stage assembly 12 and dispenser assembly 14. Wafer stage assembly 12 and dispenser assembly 14 are both motorized so that a liquid droplet of high purity de-ionized water used for the contact angle measurement can be precisely deposited at one or more particular locations on the wafer surface. Imaging software (e.g., AutoFAST Imaging software provided by AST Products) is stored on a computer 20 (e.g., a Pentium™ based system) having a video card for capturing the droplet image from camera assembly 16 and calculating the contact angle without user intervention. Specifically, the imaging software analyzes the image, pixel by pixel, and performs a droplet curve fit and baseline determination to calculate the exact contact angle.

Figure 2:
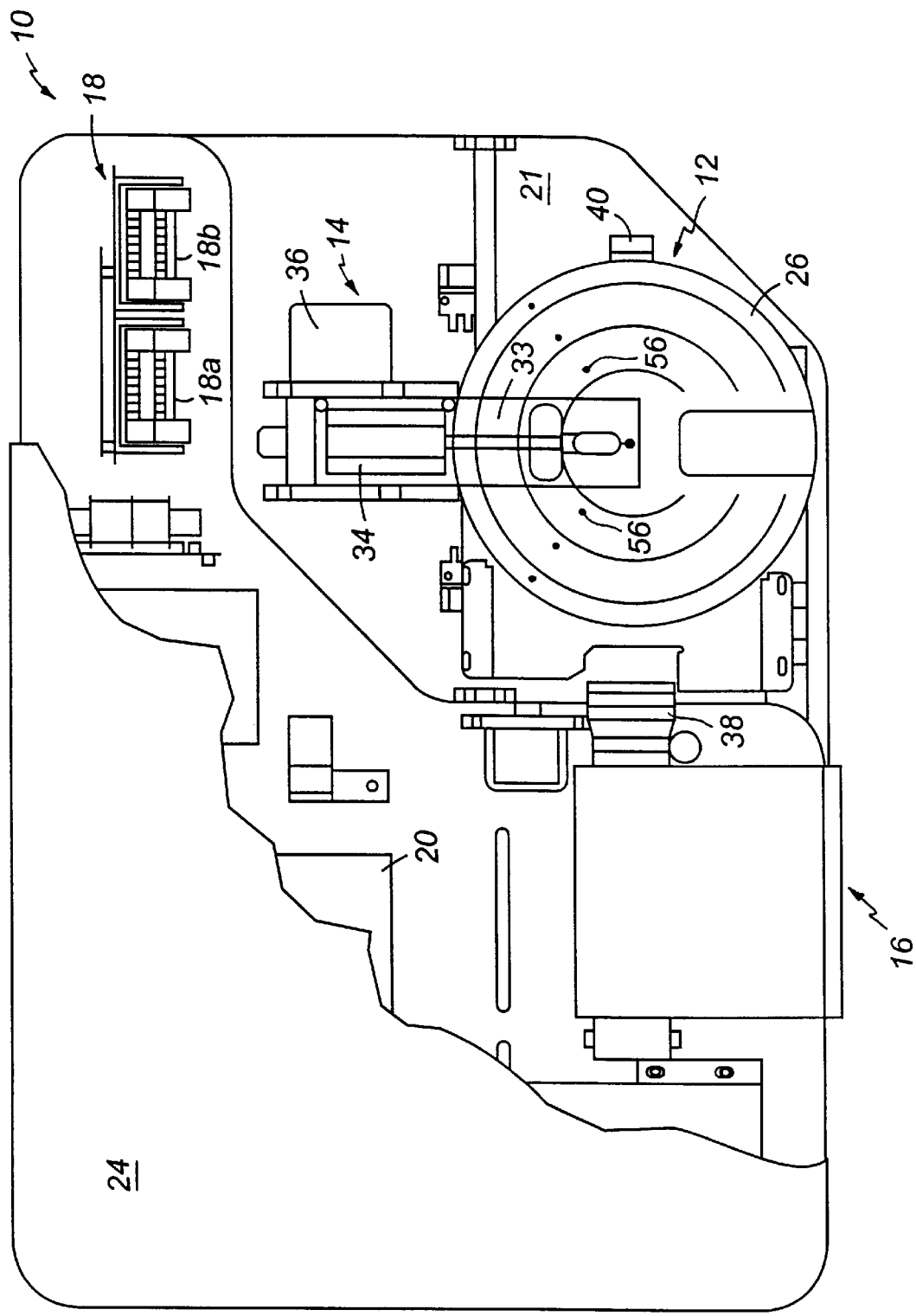
FIG. 2 is a partially cut-away top view of a portion of the surface analysis system of FIG. 1.
Figure 3:
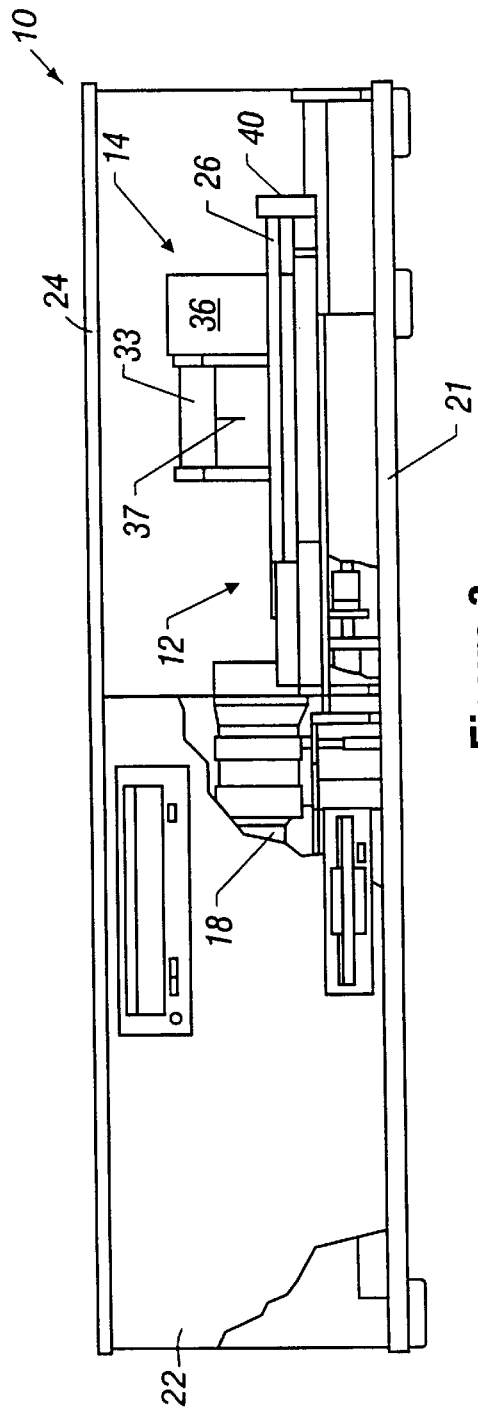
FIG. 3 is a partially cut-away side view of the surface analysis system of FIG. 2.
Figure 4:
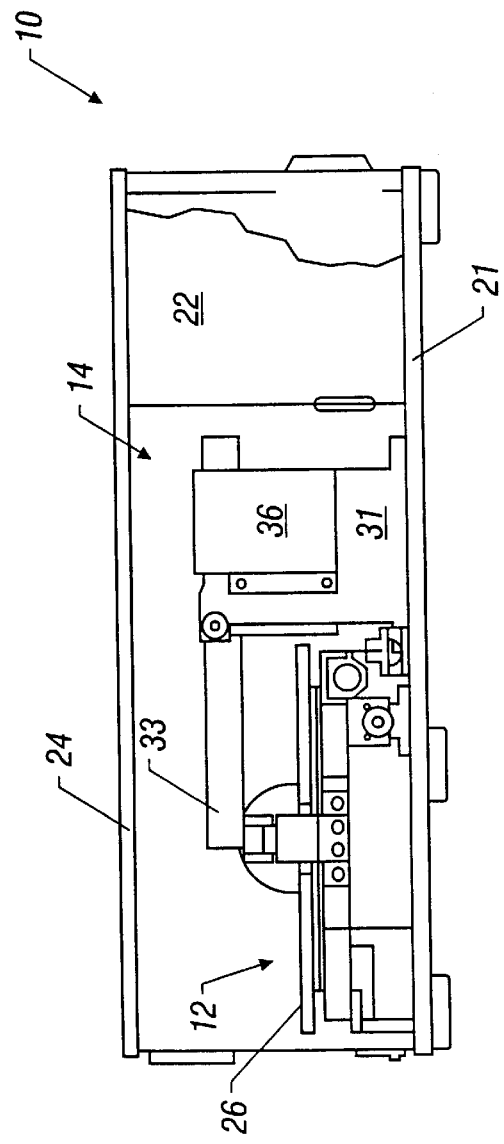
FIG. 4 is a partially cut-away end view of the surface analysis system of FIG. 2.

Referring to FIGS. 2–4, wafer surface analysis system 10 is mounted on a base plate 21 and encased within an enclosure 22 having a top 24 (shown partially cut-away in FIG. 2). Enclosure 22 provides a level of protection from dust and other particle contaminants to the above-mentioned assemblies and their components.

Figure 5:
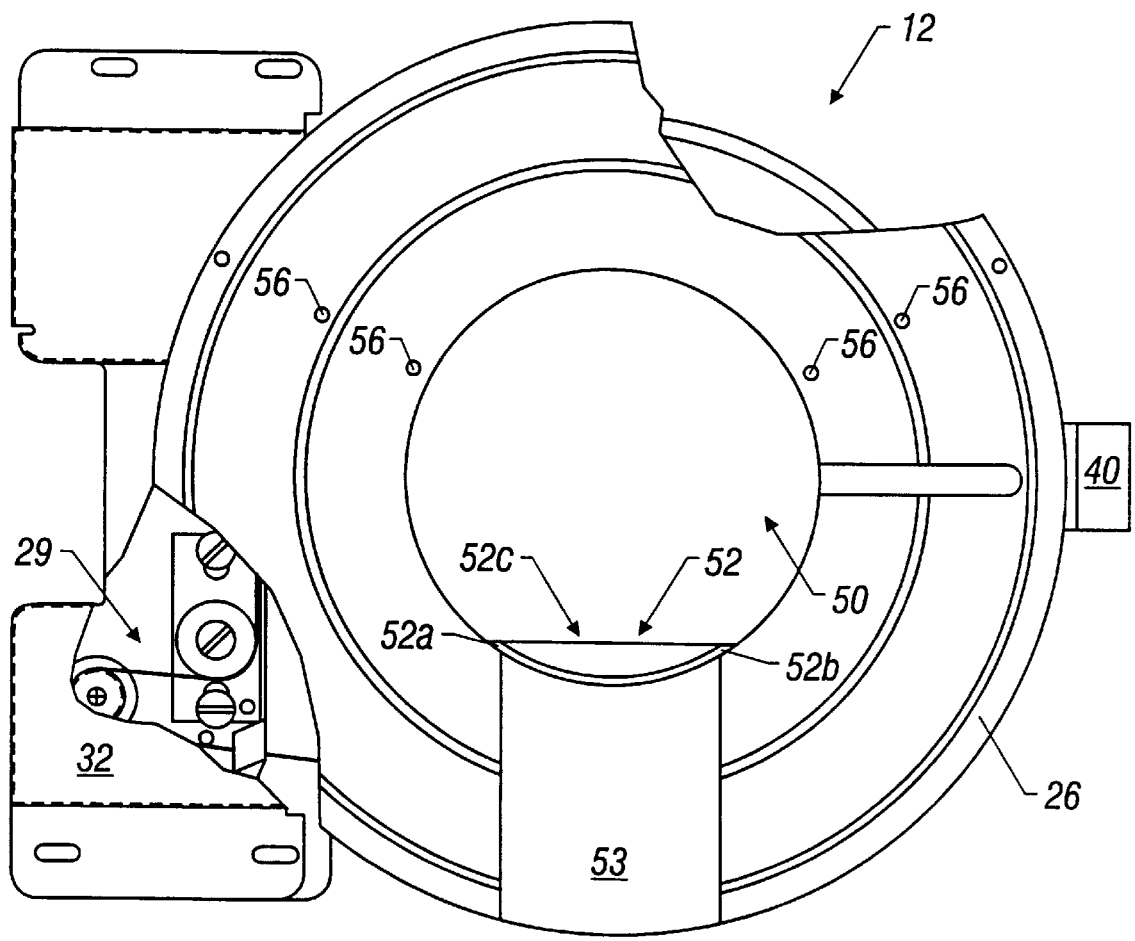
FIG. 5 is an exploded cut-away top view of the wafer stage assembly and dispenser assembly shown in FIG. 2.
Figure 6:
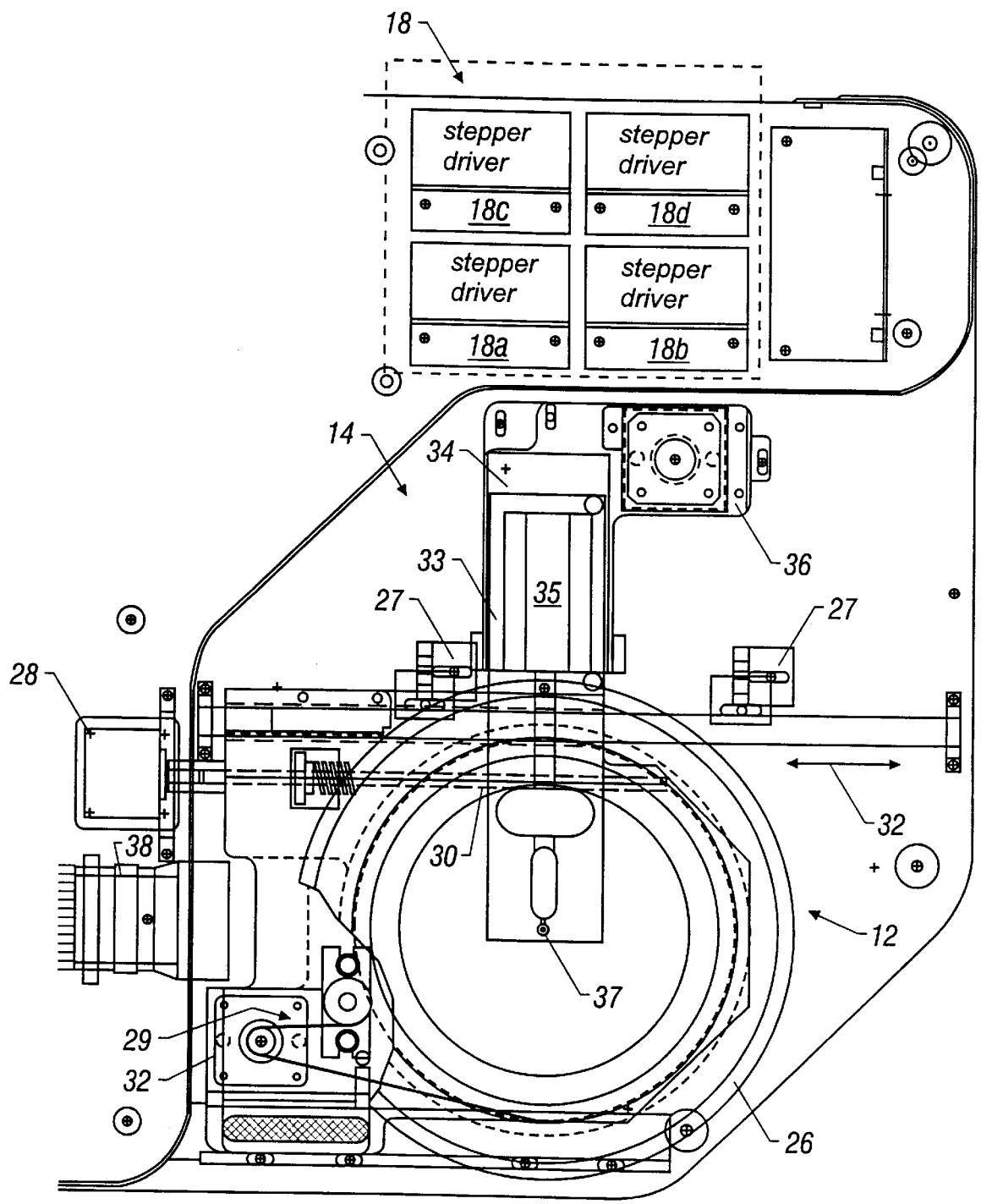
FIG. 6 is a partially cut-away top view of the wafer stage assembly.

Referring further to FIGS. 5 and 6, wafer stage assembly 12 includes a wafer chuck 26 upon which semiconductor wafers (e.g., silicon, gallium arsenide) are placed. Wafer chuck 26 is sized to receive semiconductor wafers having diameters ranging between two to twelve inches. A first stepping motor 28 is connected to wafer chuck 26 via a lead screw 30 and operates to move the wafer chuck in a horizontal direction (i.e., in a direction represented by arrow 32 shown in FIG. 6). First stepping motor 28 is used with a pair of optical switches 27 in a open-loop step control arrangement to establish the travel distance per step. A second stepping motor 32 is also connected to wafer chuck 26 via a belt and capstan mechanism 29 to allow rotating the wafer chuck a full 360 degrees. First and second stepping motors 28, 32 are electrically connected with wires (not shown) to and controlled by individual motor controllers 18a, 18b (e.g., Model No. IM483I, manufactured by Intelligent Motion Systems, Inc., Taftville, Conn.).

Figure 7:
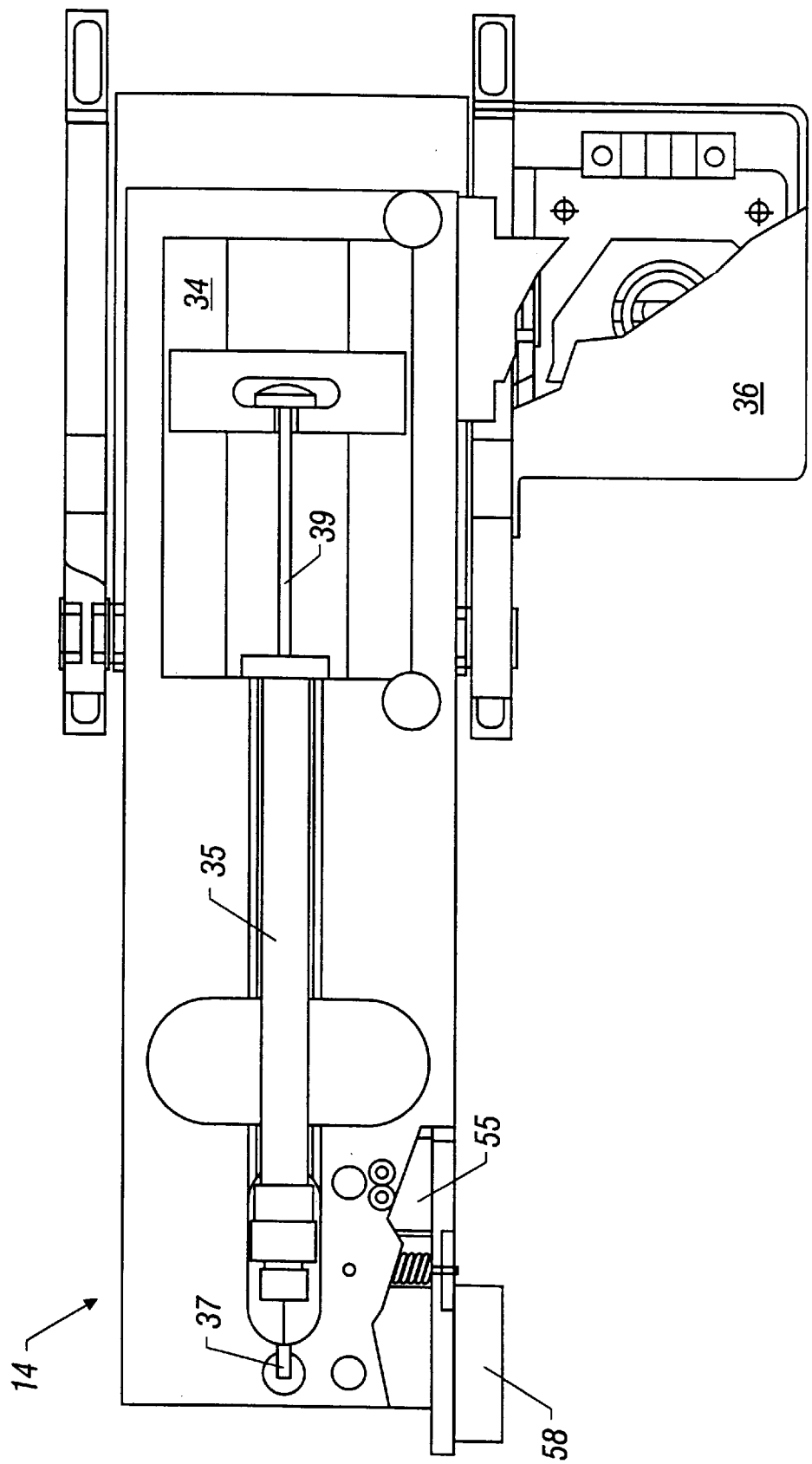
FIGS. 7 and 8 are partially cut-away top and side views, respectively, of the dispenser assembly.
Figure 8:
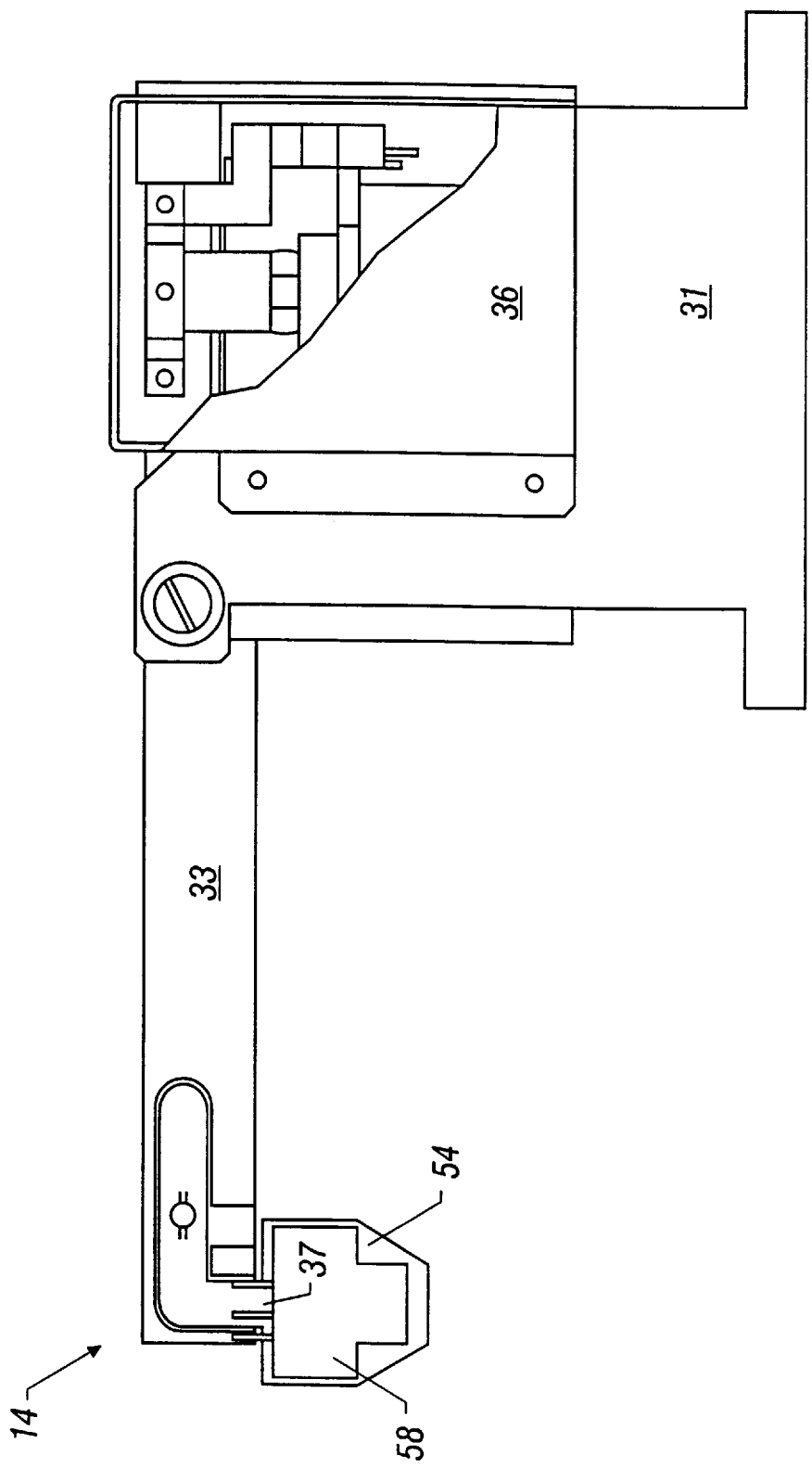

Referring to FIGS. 7–8, dispenser assembly 14 is mounted on a pedestal 31 and includes a support arm 33 within which a syringe 35 holding water is mounted. Syringe 35 extends to a tip end 37 through which water droplets are dispensed. Dispenser assembly 14 also includes third and fourth stepping motors 34, 36 which are used to dispense a water droplet onto the surface of the wafer positioned on wafer chuck 26. Third stepping motor 34 is operated to push on a plunger 39 of syringe 35 to dispense a water droplet having a precisely controlled volume (1–25 microliters). Fourth stepping motor 36 is operated to precisely pivot tip end 37 of the dispenser toward the surface of the wafer. Precise control of the amount of pivoting is important so that the controlled droplet of water dispensed from tip end 37 is transferred to, rather than dropped onto the wafer surface.

Stepping motors 28, 32, 34, 36 are of the type available from Eastern Air Devices, Dover, N.H. (Type ZB17GBK10D). Providing the proper control signals to stepping motors 28, 32, 34, 36 allows the operator to precisely deposit a water droplet onto any desired X-Y location of the surface of a wafer positioned on wafer chuck 26.

Video camera system 16 is of the type available from Pulnix America, Inc., Sunnyvale, Calif. (Model No. TM-7CN) and includes a magnification lens 38 which magnifies the droplet in a magnification range between 35× to 65× and, typically 50×. Video camera system is stationary with lens 38 pre-positioned and pre-focused to provide a magnified image of tip 35 and the surface of the wafer underlying the tip. An light emitting diode (LED) light source 40 is positioned on the side of wafer stage assembly 12, opposite that of video camera system 16 to illuminate the image area.

With reference to FIGS. 1 and 5–8, the operation of the wafer surface analysis system 10 will now be described. A wafer 50 is positioned (e.g., manually or with an automatic wafer handling system) on the center of wafer chuck 26 with the wafer's identification flat 52 roughly over a tweezer slot 53 of wafer chuck 26 (see FIG. 5). To center wafer 50 on wafer chuck 26, wafer stage assembly 12 is then rotated 90° and moved toward dispenser assembly 14. Dispenser assembly 14 is also tilted downward so that a paddle member 54 (FIG. 8) contacts the edge of identification flat 52. Wafer stage assembly 12 continues to move until wafer 50 contacts stop members 56 (FIG. 5) formed on the surface of wafer chuck 26. At this point, wafer 50 can no longer move in the horizontal direction and, in response to the further movement of wafer stage assembly 12, a force is applied to paddle member 54 closing an electrical switch 55 (FIG. 7) thereby indicating that wafer 50 is centered. Wafer stage assembly 12 then moves wafer chuck 26 away from paddle member 54 and rotates so that an infrared reflective optical sensor 58 (e.g., available from Omron Electronics, St. Charles, Ill., Model No. EE-SPY412) (FIGS. 7 and 8) mounted on dispenser assembly 14 can detect edge points 52a, 52b of identification flat 52 (FIG. 5). Having located edges 52a, 52b, wafer assembly 12 is moved to a midpoint 52c between the edges thereby establishing the diameter of wafer 50 and a rotational or "theta" reference point of wafer 50 to be examined. Wafer 50 is then held in place by vacuum applied to the underside of the wafer through wafer chuck 26. In this position, any location of wafer 50 is ready to be analyzed.

Computer 20 (FIG. 1), either under operator control or a pre-stored program, provides control signals to motor controllers 18a, 18b (FIG. 6) to move a desired position of the wafer into position under dispenser tip 37 and into the focal plane of video camera assembly 16. Computer 20 also provides control signals to motor controllers 18c, 18d (FIG. 6) to tilt support arm 33 downward and dispense a water droplet of preselected volume at the desired position of wafer surface. Attached as an Appendix is source code software for one implementation of generating the signals used to control motor controllers 18a, 18b, 18c, 18d. Dispensing tip 37 is then raised so that video camera assembly can capture a digital video image of the droplet. Computer 20 automatically analyzes image to determine the contact angle of the droplet under observation. The contact angle on both the left and right sides of the droplet, the height, width, volume and location of the droplet can be stored in the computer's memory, as well as displayed on a computer monitor.

Wafer surface analysis system 10 can be used to a single point on a wafer, or any number of operator-selected or preprogrammed points in succession without further intervention by the operator. Moreover, wafer surface analysis system can be used in conjunction with a wafer handling system to automatically several wafers in sequence.

Computer 20 may include additional software for performing statistical analysis of contact angle measurements made on a single or many wafers. For example, SPC software provided by AST Products allows the user to automatically record contact angle measurement information into an easy-to-use chart. All data, including average and standard deviation values, can be stored and exported into database manipulation software (e.g., Microsoft Excel) for further manipulation or graphing.

Other embodiments are within the claims. Although the above description relates to the characterization of semiconductor surfaces, it should be appreciated that other types of surfaces requiring a high degree of cleanliness or uniformity (e.g., magnetic disks (hard or floppy) and adhesive coatings) may also be analyzed using the wafer surface analysis system. In addition, the type of liquid dispensed on the surface of the substrate (which may be other than water) is dependent on the particular characteristic and type of substrate surface being analyzed.

```
/*
 *    File: wafrctrl.c
 *    Author: ylee
 * Company: Copyright AST Products, Inc.
 * $Source$
 * $Id$
 */ include"master.h"

define CHAR_TIME    10 define PI  3.141592654 define EnableItem( hDlg, item, enable ) \
EnableWindow( GetDlgItem( hDlg, item ), enable )

extern void
CenterDialog (HWND hDlg) ;

extern int
SendCommand(int idDev, int nFields, char cName,
        char cCmd, int nField1, int nField2);
extern int
SendStrCommand (int idDev, char cName, LPSTR p);

extern void Wait (DWORD WaitTime) ;

extern LPSTR
LocateStr (LPSTR p, LPSTR q);

extern int
StrToReal (LPSTR pStr, double * rsp, BOOL bPt);

extern BOOL
OpenCommPort(int iPort);

extern int
CloseCommPort(int iCommDev);

extern HANDLE hInst;
extern HWND hWndMDIClient, hWndFrame;
extern char szBuffer[];
extern CALCDATA CalcData;
extern HWND hWndScriptRunner, hWndLocator ;
extern int   idCommDev ;
extern char szControlCmd[SIZEOFBUFFER];
extern char szResponse[SIZEOFBUFFER];

// Control related variables
// IMS commands
extern int bPartyMode ;
extern int nCommPort ;
extern char cJogSpeed ;
extern char cCurrents ;
extern char cSlewRate ;
extern char cFindHome ;
extern char cSetOrigin ;
extern char cTransmit ;
extern char cEscape ;
extern char cResetAll ;
```

1

```
extern char szReadPosition[8];
extern char szReadSwitch[8];
extern char szSetLimit[8];
extern DWORD tCharTime ;

extern char cSyringeName ;
extern char cTiltName ;
char cRotateName ;
char cXName ;
extern double dVolumePerStep ;
extern int SyringeSpeed[3];
extern int SyRefillSpeed ;
extern int nSyringeSize;
extern int nSyringeSpeed;
extern int nSyringeDirection ;
extern double dDropletSize ;
extern double dSyringeSteps;
extern char szSpeed[] ;
extern char szSYType[3][7];
extern double dFactor[3] ;

typedef struct
{
  DOUBLEPNT pt ;
  int angle ;
} VCA3KDATA ;

DOUBLEPNT           // Orig: 0,0    x, y range: 0 ~ 1
NormalizePnt (DOUBLEPNT Pnt, DOUBLEPNT Cntr, double radi)
{
  Pnt.x = (Pnt.x- Cntr.x) / radi   ;
  Pnt.y = (Pnt.y- Cntr.y) / radi   ;
  return Pnt ;
}

DOUBLEPNT
DeNormalizePnt (DOUBLEPNT Pnt, DOUBLEPNT Cntr, double radi)
{
  Pnt.x = (Pnt.x*radi+Cntr.x) ;
  Pnt.y = (Pnt.y*radi+Cntr.y) ;
  return Pnt ;
}

POLAR GetPolar(DOUBLEPNT dPnt)
{
  POLAR polarPnt ;

if (dPnt.x==0 && dPnt.y==0)
    {
      polarPnt.r = 0 ;
      polarPnt.theta = 0;
    }
  else
    {
      polarPnt.r = sqrt( (dPnt.x*dPnt.x + dPnt.y*dPnt.y) );
      polarPnt.theta = atan2(dPnt.y,dPnt.x);
    }
  return polarPnt ;
}

POLAR
GetDisplacement (DOUBLEPNT init, DOUBLEPNT end) [2]
```

```
{
  POLAR Pnt1, Pnt2, Delta;

Pnt1 = GetPolar(init);
  Pnt2 = GetPolar(end);

Delta.r = (Pnt2.r - Pnt1.r);
  Delta.theta = (Pnt2.theta - Pnt1.theta) ;

if ( Delta.theta > PI && Delta.theta < 2*PI )
    Delta.theta = -(2*PI - Delta.theta) ;
  if ( Delta.theta > -2*PI && Delta.theta < -PI )
    Delta.theta = 2*PI + Delta.theta ;
  Delta.theta = Delta.theta*180/PI ;
  return Delta;
}

BOOL
IsMotorMoving ( char cMotor )
{
  LPSTR p;
  double rsp;

SendCommand(idCommDev, 0, cMotor, '^',0,0);
  p = LocateStr(szResponse, "^");
  if (*p && StrToReal(p, &rsp, TRUE) && ((int)rsp==0)) return(FALSE);
  return(TRUE);
}

BOOL
IsHomeYet ( char cMotor,char cSW ) // cSW={A:Limit A, B:Limit B, H:Home SW}
{
    LPSTR p;
    double rsp;

switch(cSW)
      {
      case 'A':
      case 'B':
        SendCommand(idCommDev, 1, cMotor, ']',0,0);
        p = LocateStr(szResponse, "0");
        break;
      case 'H':
        SendCommand(idCommDev, 1, cMotor, ']',1,0);
        p = LocateStr(szResponse, "1");
        break ;
      }
    switch(cSW)
      {
      case 'H':
      case 'A':
        if (*p && StrToReal(p, &rsp, TRUE) && ((int)rsp==1))
      return(TRUE);
        return(FALSE) ;
      case 'B':
        if (*p && StrToReal(p, &rsp, TRUE) && ((int)rsp==2))
      return(TRUE);
        return(FALSE) ;

default:
        return(FALSE) ;
      }
```

```c
} double ReadPosition (char cMotor)
{
  double dPosition ;
  LPSTR p ;

SendStrCommand(idCommDev, cMotor, (LPSTR)szReadPosition);
  p=LocateStr(szResponse, szReadPosition);
  StrToReal(p, &dPosition, TRUE);
  return dPosition ;
}

BOOL InitMotors ( HANDLE hDlg )
{
  char* szErrStr[128] ;
  BOOL bError=FALSE ;

//initialize com port and setup motors
  cRotateName = (char) GetPrivateProfileInt("WINVCA",
                                            "Ctrl_Rotate",82,
                                            "WINVCA.INI");
  cSyringeName = (char) GetPrivateProfileInt("WINVCA",
                                             "Ctrl_Syringe", 83,
                                             "WINVCA.INI");
  cTiltName = (char) GetPrivateProfileInt("WINVCA",
                                          "Ctrl_Tilt",84,
                                          "WINVCA.INI");
  cXName = (char) GetPrivateProfileInt("WINVCA",
                                       "Ctrl_X",88,
                                       "WINVCA.INI");
  if (idCommDev < 0)
    if(!OpenCommPort(nCommPort))   return FALSE;

SendCommand(idCommDev,3,0,cResetAll,0,0);
  if (SendCommand(idCommDev,4,cSyringeName,0,0,0)!=0)
    {
       SendCommand(idCommDev,3,0,cResetAll,0,0);
       bError=TRUE ;
       wsprintf((LPSTR)szErrStr,"Syringe Controller") ;
    }
  if (SendCommand(idCommDev,4,cTiltName,0,0,0)!=0)
    {
       SendCommand(idCommDev,3,0,cResetAll,0,0);
       bError=TRUE ;
       wsprintf((LPSTR)szErrStr,"%s, %s", (LPSTR)szErrStr, "Tilt Controller") ;
    }
  if (SendCommand(idCommDev,4,cRotateName,0,0,0)!=0)
    {
       SendCommand(idCommDev,3,0,cResetAll,0,0);
       bError=TRUE ;
       wsprintf((LPSTR)szErrStr,"%s, %s", (LPSTR)szErrStr, "Rotation Controller") ;
    }
  if (SendCommand(idCommDev,4,cXName,0,0,0)!=0)
    {
       SendCommand(idCommDev,3,0,cResetAll,0,0);
       bError=TRUE ;
       wsprintf((LPSTR)szErrStr,"%s, %s",(LPSTR)szErrStr,"Stage X-axis Controller") ;
    }
  if (bError)
    {
       wsprintf((LPSTR)szErrStr,"%s %s", (LPSTR)szErrStr, "not responding!") ;
       MessageBox(hDlg, (LPSTR)szErrStr, "Motor ERROR", MB_OK|MB_ICONEXCLAMATION);
```

```c
        idCommDev = CloseCommPort(idCommDev);
        return FALSE ;
     }
  SendCommand(idCommDev,1,cSyringeName,cSlewRate, DEF_R_SLEW,0);
  SendCommand(idCommDev,2,cSyringeName,cCurrents,0,DEF_S_RUN_CURR);

SendCommand(idCommDev,1,cTiltName,cSlewRate, DEF_T_SLEW,0);   // Set current locks up small mo
tor,
  SendCommand(idCommDev,2,cTiltName,cCurrents,0,DEF_T_RUN_CURR);// big one works ok !!??

SendCommand(idCommDev,1,cRotateName,cSlewRate, DEF_R_SLEW,0);
  SendCommand(idCommDev,2,cRotateName,cCurrents,0,DEF_R_RUN_CURR) ;

SendCommand(idCommDev,1,cXName,cSlewRate, DEF_X_SLEW,0);
  SendCommand(idCommDev,2,cXName,cCurrents,0,DEF_X_RUN_CURR) ;

return TRUE ;
} void DrawGrid (HDC hDC, POINT ptCenter, int nRadius, int nWaferSize)
{
  int i, nGridSize ;

Ellipse(hDC, ptCenter.x-nRadius, ptCenter.y-nRadius,
          ptCenter.x+nRadius, ptCenter.y+nRadius);

nGridSize = 10*nRadius/(nWaferSize/2) ; // 10mm
  for ( i = 0 ; i < nRadius ; i=i+nGridSize)
    {
      int j ;
      j = (int) sqrt(((double)nRadius*(double)nRadius)-((double)i*(double)i));
      // vertical
      MoveTo(hDC, ptCenter.x+i, ptCenter.y+j); LineTo(hDC, ptCenter.x+i, ptCenter.y-j);
      MoveTo(hDC, ptCenter.x-i, ptCenter.y+j); LineTo(hDC, ptCenter.x-i, ptCenter.y-j);
      // horizontal
      MoveTo(hDC, ptCenter.x+j, ptCenter.y+i); LineTo(hDC, ptCenter.x-j, ptCenter.y+i);
      MoveTo(hDC, ptCenter.x+j, ptCenter.y-i); LineTo(hDC, ptCenter.x-j, ptCenter.y-i);
    }
} int CenterWafer()
{
  int i ;
  int nWaferSize=0;
  int nPosition ;
  double dRadiusDetected ;

if (! IsHomeYet(cTiltName,'A'))
    SendCommand(idCommDev,2, cTiltName, cFindHome, DEF_T_FINDHOME, 0) ;
  if (! IsHomeYet(cXName,'B'))
    SynchroFindLimit(cXName, 'B', DEF_X_FINDHOME) ;
  SendCommand(idCommDev,0, cXName, cSetOrigin, 0, 0) ;
  i = GetPrivateProfileInt("WINVCA","Sensor_Steps", DEF_SENSOR_STEPS,"WINVCA.INI");
  SynchroMove(cTiltName, '-', i) ;
  SynchroFindHome(cRotateName, '+', DEF_R_FINDHOME) ;
  SynchroMove(cRotateName, '-', (int)(90/DEF_R_RATIO));
  SynchroMove(cTiltName, '-', 175);
  SynchroFindHome(cXName, '+', DEF_X_SLEW) ;
  nPosition = (int)ReadPosition(cXName) ;
  dRadiusDetected=DEF_CENTER_TO_SPOT-((nPosition*DEF_X_RATIO*25.4)-DEF_PEDAL_TO_SENSOR) ;
  if(dRadiusDetected<=40 || dRadiusDetected>=105) return(nWaferSize) ;   // error occurs
  else
```

```
      {
        if(dRadiusDetected<105 && dRadiusDetected>90)   nWaferSize = 200 ;
        if(dRadiusDetected< 80 && dRadiusDetected>65)   nWaferSize = 150 ;
        if(dRadiusDetected< 55 && dRadiusDetected>40)   nWaferSize = 100 ;
        if(nWaferSize==0) return(nWaferSize) ;           // doesn't match any sizes
        SendCommand(idCommDev, 1, cXName, 'A', 56, 0) ;  // turn on valve
        i=(int)(((nWaferSize/2-dRadiusDetected+DEF_PEDAL_TO_SENSOR)/25.4)/DEF_X_RATIO) ;
        SynchroMove(cXName, '-', i) ;       // move the sensor to the edge of wafer
        SynchroMove(cTiltName, '+', 175); // move sensor to normal height
        return(nWaferSize);
      }
}

BOOL FindNotch()
{
  double dPosition;

SynchroFindHome(cRotateName, '+', 300);
  SendCommand(idCommDev,0,cRotateName, cSetOrigin, 0,0);
  SynchroFindHome(cRotateName, '-', 300);
  dPosition = ReadPosition(cRotateName) ;
  SendCommand(idCommDev,1,cRotateName, '+',(int) fabs(dPosition)/2,0);
  sprintf(szBuffer, "Distance=%d", (int)dPosition) ;
  MessageBox(NULL,szBuffer,NULL, MB_OK) ;
  SendCommand(idCommDev,1,cRotateName, '+',(int)(90/DEF_R_RATIO), 0);
  return TRUE;
}

BOOL SynchroMove(char cMotor, char cDir, int nSteps)
{
  int nTimeOut=0, nTarget;
  const int nTimeOutLimit=10000;

if(cDir=='+')
    nTarget =  (int)ReadPosition(cMotor) + nSteps ;
  else
    nTarget =  (int)ReadPosition(cMotor) - nSteps ;
  SendCommand(idCommDev, 1, cMotor, cDir, nSteps, 0) ;

while((nTimeOut<nTimeOutLimit)&&(nTarget!=(int)ReadPosition(cMotor)))
     {
       nTimeOut++;
       Wait((DWORD)10);
     }
  if (nTimeOut>=nTimeOutLimit) return FALSE;
  return TRUE;
}

BOOL SynchroFindHome(char cMotor, char cDir, int nSpeed)
{
  int nTimeOut=0;
  const int nTimeOutLimit=10000;
  if (!IsHomeYet(cMotor, 'H'))
     {
       switch(cDir)
       {
       case '-': SendCommand(idCommDev,2,cMotor, cFindHome, nSpeed,1); break;
       case '+': SendCommand(idCommDev,2,cMotor, cFindHome, nSpeed,0); break;
       }
       while((nTimeOut<nTimeOutLimit)&&(!IsHomeYet(cMotor, 'H')))
       {
         nTimeOut++;
         Wait((DWORD)10);
```

```
      if(!IsMotorMoving(cMotor))
        {
          switch(cDir)
        {
        case '-': SendCommand(idCommDev,1,cMotor, '-', 1,0); break;
        case '+': SendCommand(idCommDev,1,cMotor, '+', 1,0); break;
        }
        }
    }
      if (nTimeOut>=nTimeOutLimit) return FALSE;
    }
  return TRUE;
}

BOOL SynchroFindLimit(char cMotor, char cSW, int nSpeed)
{
  int nTimeOut=0;
  const int nTimeOutLimit=10000;
  if (!IsHomeYet(cMotor, cSW))
    {
      switch(cSW)
    {
    case 'A': SendCommand(idCommDev,2,cMotor, cFindHome, nSpeed,0);  break;
    case 'B': SendCommand(idCommDev,2,cMotor, cFindHome, nSpeed,1);  break;
    case 'H': SendCommand(idCommDev,2,cMotor, cFindHome, nSpeed,0);  break;
    }
      while((nTimeOut<nTimeOutLimit)&&(!IsHomeYet(cMotor, cSW)))
    {
      nTimeOut++;
      Wait((DWORD)10);
      if(!IsMotorMoving(cMotor))
        {
          switch(cSW)
        {
        case 'A': SendCommand(idCommDev,1,cMotor, '+', 1,0); break;
        case 'B': SendCommand(idCommDev,1,cMotor, '-', 1,0); break;
        case 'H': SendCommand(idCommDev,1,cMotor, '+', 1,0); break;
        }
        }
    }
      if (nTimeOut>=nTimeOutLimit) return FALSE;
    }
  return TRUE;
}

BOOL FAR PASCAL __export
HWDiagDlg (HWND hDlg, unsigned message,
       WORD wParam, LONG lParam)
{
  static BYTE Status=0x0000 ;
  int WaitTime=10;

switch (message)
    {
    case WM_INITDIALOG:
      {
      extern WORD wCapMode ;
      extern HWND hWndLiveVideo, hWndPreview;
      CenterDialog(hDlg) ;
      wCapMode = WE_FREEZE;      // stop live video
      SetWindowText(hWndLiveVideo, (LPSTR)"Frozen Video");
      SetDlgItemText(hWndPreview, IDFREEZE, "&Live");
      LoadString(hInst, IDS_HWDIAG_INIT, szBuffer,[7] SIZEOFBUFFER);
```

```
SetDlgItemText(hDlg, IDC_EDIT1, (LPSTR) szBuffer );
return TRUE ;
   }
case WM_SYSCOMMAND:
  if ( wParam == SC_CLOSE)
{ EndDialog (hDlg, TRUE); return TRUE ; }
  break ;

case WM_COMMAND:
  switch (wParam)
{
case IDOK:
   {
      int nPosition ;
      if(!(Status&0x0001))
         {
         Status=Status|0x0001 ;
         LoadString(hInst, IDS_HWDIAG_X, szBuffer, SIZEOFBUFFER);
         SetDlgItemText(hDlg, IDC_EDIT1, (LPSTR) szBuffer );
         return TRUE;
         }
      if (!(Status&0x0002))
         {
         SetCursor(LoadCursor(NULL, IDC_WAIT));
         if(SynchroFindLimit(cXName, 'A', 1000))
            WritePrivateProfileString("HardwareInfo", "X-Axis_SW_A",
                        "1", "WINVCA.INI");
         else
            WritePrivateProfileString("HardwareInfo", "X-Axis_SW_A",
                        "0", "WINVCA.INI");
         SendCommand(idCommDev,0,cXName, cSetOrigin, 0,0);
         if(SynchroFindLimit(cXName, 'B', 1000))
            WritePrivateProfileString("HardwareInfo", "X-Axis_SW_B",
                        "1", "WINVCA.INI");
         else
            WritePrivateProfileString("HardwareInfo", "X-Axis_SW_B",
                        "0", "WINVCA.INI");
         nPosition = (int)fabs(ReadPosition(cXName)) ;
         wsprintf ((LPSTR)szBuffer, "%d", nPosition);
         WritePrivateProfileString("HardwareInfo", "X-Axis_Steps",
                        szBuffer, "WINVCA.INI");
         Status=Status|0x0002 ;
         SetCursor(LoadCursor(NULL, IDC_ARROW));
         LoadString(hInst, IDS_HWDIAG_R, szBuffer, SIZEOFBUFFER);
         SetDlgItemText(hDlg, IDC_EDIT1, (LPSTR) szBuffer );
         return TRUE ;
         }
      if (!(Status&0x0004))
         {
         double dTmp ;
         SetCursor(LoadCursor(NULL, IDC_WAIT));

dTmp = GetPrivateProfileDouble("WINVCA","R_Ratio",
                           DEF_R_RATIO, "WINVCA.INI");
         nPosition=(int)(360/dTmp);
         SendCommand(idCommDev,0,cRotateName, cSetOrigin, 0, 0);
         SendCommand(idCommDev,2,cRotateName, '+', nPosition, 0);
         while(nPosition!=(int)fabs(ReadPosition(cRotateName)))
            Wait((DWORD)WaitTime);
         Status=Status|0x0004 ;
         SetCursor(LoadCursor(NULL, IDC_ARROW));
         SetCursor(LoadCursor(NULL, IDC_WAIT));
         LoadString(hInst, IDS_HWDIAG_T, szBuffer, SIZEOFBUFFER);
```

```c
      return TRUE ;
    }
  if (!(Status&0x0008))
    {
    SetCursor(LoadCursor(NULL, IDC_WAIT));
    if(SynchroFindLimit(cTiltName, 'A', 200))
      WritePrivateProfileString("HardwareInfo", "T-Axis_SW_A",
                    "1", "WINVCA.INI");
    else
      WritePrivateProfileString("HardwareInfo", "T-Axis_SW_A",
                    "0", "WINVCA.INI");
    SendCommand(idCommDev,0,cTiltName, cSetOrigin, 0,0);
    if(SynchroFindLimit(cTiltName, 'B', 200))
      WritePrivateProfileString("HardwareInfo", "T-Axis_SW_B",
                    "1", "WINVCA.INI");
    else
      WritePrivateProfileString("HardwareInfo", "T-Axis_SW_B",
                    "0", "WINVCA.INI");
    nPosition = (int)fabs(ReadPosition(cTiltName)) ;
    wsprintf ((LPSTR)szBuffer, "%d", nPosition);
    WritePrivateProfileString("HardwareInfo", "T-Axis_Steps",
                  szBuffer, "WINVCA.INI");
    Status=Status|0x0008 ;
    SetCursor(LoadCursor(NULL, IDC_ARROW));
    LoadString(hInst, IDS_HWDIAG_S, szBuffer, SIZEOFBUFFER);
    SetDlgItemText(hDlg, IDC_EDIT1, (LPSTR) szBuffer );
    return TRUE ;
    }
  if (!(Status&0x00010))
    {
    SetCursor(LoadCursor(NULL, IDC_WAIT));
    if(SynchroFindLimit(cSyringeName, 'A', 1000))
      WritePrivateProfileString("HardwareInfo", "S-Axis_SW_A",
                    "1", "WINVCA.INI");
    else
      WritePrivateProfileString("HardwareInfo", "S-Axis_SW_A",
                    "0", "WINVCA.INI");
    SendCommand(idCommDev,0,cSyringeName, cSetOrigin, 0,0);
    if(SynchroFindLimit(cSyringeName, 'B', 1000))
      WritePrivateProfileString("HardwareInfo", "S-Axis_SW_B",
                    "1", "WINVCA.INI");
    else
      WritePrivateProfileString("HardwareInfo", "S-Axis_SW_B",
                    "0", "WINVCA.INI");
    nPosition = (int)fabs(ReadPosition(cSyringeName)) ;
    wsprintf ((LPSTR)szBuffer, "%d", nPosition);
    WritePrivateProfileString("HardwareInfo", "S-Axis_Steps",
                  szBuffer, "WINVCA.INI");
    Status=Status|0x00010 ;
    SetCursor(LoadCursor(NULL, IDC_ARROW));
    }
  LoadString(hInst, IDS_HWDIAG_FINISH, szBuffer, SIZEOFBUFFER);
  SetDlgItemText(hDlg, IDC_EDIT1, (LPSTR) szBuffer );
  SetDlgItemText(hDlg, IDCANCEL, (LPSTR) "&Finish" );
  EnableWindow(GetDlgItem( hDlg, IDOK), FALSE)  ;
  break ;

case IDCANCEL:
  //WritePrivateProfileString("WINVCA", "Not_Show_Spc_Mesg",
  //"No", "WINVCA.INI");
  EndDialog (hDlg, TRUE);  break ;
  }
}
```

```
  ;
  return FALSE ;
}
////////////////////////////////////////////////////////////////////
/////////////////////////////////// Control Sequence Link List Definition
//  members in each element of list
typedef struct
{
  char ID ;           // Control ID  B reserved for Button control
                      //              M reserved for SendMessage()
  int  nField ;       // number of fields
  char Command ;      // Motor Command to be sent
  int  Data1 ;        // (1st data for Motor),(BtnID for  Button control)
                      // (SendMessage-uMsg)
  int  Data2 ;        // (2nd data for Motor),(Enable/Disable for Button ctrl)
                      // (SendMessage-wParam)
  BOOL Wait ;         // Wait for *PREVIOUS* Motor commands to complete?
  HANDLE hNext ;
} ACTION, * pACTION;
////////////////////////////////////////////////////////////////
////   phHead: Pointer of Handle to the head of link list
////   To initialize a new list set hHead = NULL
////   Function returns FALSE if memory allocation failed
BOOL AddAction( HANDLE* phHead, char ID, int  nField, char Cmd, int Data1, int Data2, BOOL Wait)

{
  HANDLE hCur=*phHead, hNew ;
  pACTION pCur, pNew ;

if (*phHead == NULL)       /// creates the first element
    {
      hNew = LocalAlloc( LMEM_MOVEABLE, sizeof(ACTION) ) ;
      if (hNew != NULL) *phHead = hNew ;
      else return FALSE ;
      pNew = (pACTION) LocalLock(hNew) ;
      if (pNew == NULL) return FALSE ;
      pNew->ID = ID ;
      pNew->nField = nField ;
      pNew->Command = Cmd ;
      pNew->Data1 = Data1 ;
      pNew->Data2 = Data2 ;
      pNew->Wait = Wait ;
      pNew->hNext = NULL ;
      LocalUnlock(hNew) ;
      return TRUE ;
    }
  else
    {
      while ( (pCur=(pACTION)LocalLock(hCur))->hNext != NULL )
         {                               /// loop until end of list
           hNew = pCur->hNext ;
           LocalUnlock(hCur) ;
           hCur = hNew ;
         }
      hNew = LocalAlloc( LMEM_MOVEABLE, sizeof(ACTION)) ;
      if (hNew != NULL)  pCur->hNext = hNew ;
      else return FALSE ;
      LocalUnlock(hCur) ;

pNew = (pACTION) LocalLock(hNew) ;
      if (pNew == NULL) return FALSE ;
      pNew->ID = ID ;
```

```
        pNew->nField = nField ;
        pNew->Command = Cmd ;
        pNew->Data1 = Data1 ;
        pNew->Data2 = Data2 ;
        pNew->Wait = Wait ;
        pNew->hNext = NULL ;
        LocalUnlock(hNew) ;
        return TRUE ;
     }
}
////////////////////////////////////////////////////
////    phHead: Pointer of Handle to the head of link list
////    To initialize a new list set hHead = NULL
////    Function returns FALSE if memory allocation failed
BOOL AddBtnCtrl( HANDLE* phHead, int BtnID, int Enable)
{
  return AddAction( phHead,
                    'B',
             0,
                    '\0',
                    BtnID,
                    Enable,
                    FALSE) ;
}
////////////////////////////////////////////////////
////    phHead: Pointer of Handle to the head of link list
////    To initialize a new list set hHead = NULL
////    Function returns FALSE if memory allocation failed
BOOL AddMsgCtrl( HANDLE* phHead, int uMsg, int wParam, BOOL Wait, char Extra)
{
  return AddAction( phHead,
                    'M',
             0,
                    Extra,
                    uMsg,
                    wParam,
                    Wait) ;
}
////////////////////////////////////////////////////
// Function passes the first ACTION to pResult
// and frees that memory in the list
// Function returns FALSE if error occurs
BOOL GetNextAction (HANDLE* phHead, pACTION pResult )
{
  HANDLE hCur = *phHead ;
  pACTION pCur ;

if( *phHead == NULL )
    {
       pResult = NULL ;
       return FALSE ;
    } pCur = (pACTION) LocalLock( hCur ) ;
  pResult->ID       = pCur->ID ;
  pResult->nField   = pCur->nField ;
  pResult->Command  = pCur->Command;
  pResult->Data1    = pCur->Data1 ;
  pResult->Data2    = pCur->Data2 ;
  pResult->Wait     = pCur->Wait ;
  *phHead           = pCur->hNext ; // update hHead
  LocalUnlock(hCur) ;
  LocalFree(hCur) ;                 // Free memory
```

```c
    return TRUE ;
}
/////////////////////////////////////////////////////
// Function passes the first ACTION to pResult
// Function returns FALSE if error occurs
BOOL PeekNextAction (HANDLE* phHead, pACTION pResult )
{
  pACTION pHead ;

if( *phHead == NULL )
    {
      pResult = NULL ;
      return FALSE ;
    }
  pHead = (pACTION) LocalLock( *phHead ) ;
  pResult->ID      = pHead->ID ;
  pResult->nField  = pHead->nField ;
  pResult->Command = pHead->Command;
  pResult->Data1   = pHead->Data1 ;
  pResult->Data2   = pHead->Data2 ;
  pResult->Wait    = pHead->Wait ;
  LocalUnlock(*phHead) ;
  return TRUE ;
}
///// End of Action Link List Definition
/////////////////////////////////////////////////////////////////////
#define POSITIVE 0
#define SW_A_DIR 0
#define NEGATIVE 1
#define SW_B_DIR 1
typedef struct
{
  char cName;
  BOOL bMov ;
  char cCmd ;
  int  nDir ;
  int  nCur ;
  int  nEnd ;
  int  nTry ;
} MOTORINFO, FAR* LPMOTORINFO ;

UINT StartSequence( HANDLE hDlg )
{
  return SetTimer(hDlg, ACTION_TIMER, 250,NULL ) ;
} void StartMotor(HWND hDlg, LPMOTORINFO lpMotorInfo, int TIMER_ID, ACTION CurAct)
{
  lpMotorInfo->cName = CurAct.ID;
  lpMotorInfo->bMov  = TRUE ;
  lpMotorInfo->cCmd  = CurAct.Command ;
  lpMotorInfo->nCur  = (int)ReadPosition(lpMotorInfo->cName) ;
  lpMotorInfo->nTry  = 0 ;
  if(lpMotorInfo->cCmd == cFindHome) lpMotorInfo->nDir = CurAct.Data2 ; // SW A or B
  else if(lpMotorInfo->cCmd=='+')
    { lpMotorInfo->nDir = POSITIVE ; lpMotorInfo->nEnd = lpMotorInfo->nCur + CurAct.Data1 ; }
  else if(lpMotorInfo->cCmd=='-')
    { lpMotorInfo->nDir = NEGATIVE ; lpMotorInfo->nEnd = lpMotorInfo->nCur - CurAct.Data1 ; }
  SendCommand(idCommDev, CurAct.nField, CurAct.ID, CurAct.Command, CurAct.Data1, CurAct.Data2);
  SetTimer(hDlg, TIMER_ID, 250,NULL ) ;
}

BOOL CheckMotorStatus(HWND hDlg, LPMOTORINFO lpMotorInfo, int TIMER_ID)
```

```
{
  char* szMesg[255] ;
  lpMotorInfo->nTry++ ;
  switch(lpMotorInfo->cCmd)
     {
     case '+':
     case '-':      // Move command
        {
     lpMotorInfo->nCur = (int)ReadPosition(lpMotorInfo->cName) ;
     if(lpMotorInfo->nEnd == lpMotorInfo->nCur)
        {KillTimer(hDlg, TIMER_ID);  lpMotorInfo->bMov=FALSE; return TRUE;}
     else if((IsHomeYet(lpMotorInfo->cName, 'A') && lpMotorInfo->nDir== SW_A_DIR)||
          (IsHomeYet(lpMotorInfo->cName, 'B') && lpMotorInfo->nDir== SW_B_DIR) )
        {
        KillTimer(hDlg, TIMER_ID) ;
        lpMotorInfo->bMov=FALSE;
        LoadString(hInst, IDS_REACH_LIMIT_SW, szBuffer, SIZEOFBUFFER);
        wsprintf((LPSTR)szMesg, "%c motor %s", lpMotorInfo->cName, szBuffer) ;
        MessageBox(hDlg, (LPSTR)szMesg, "Warning", MB_OK|MB_ICONEXCLAMATION);
        return TRUE ;
        }
     break ;
        }
     case 'F':
        {
     if(lpMotorInfo->cName == cRotateName)
        {
        if ( IsHomeYet(lpMotorInfo->cName, 'H') )
           {KillTimer(hDlg, TIMER_ID); lpMotorInfo->bMov=FALSE; return TRUE;}
        else
           {
        if(!IsMotorMoving(lpMotorInfo->cName))
           {
           SendCommand(idCommDev,1,lpMotorInfo->cName,'+',2,0) ;
           if( IsHomeYet(lpMotorInfo->cName, 'H'))
              {KillTimer(hDlg, TIMER_ID); lpMotorInfo->bMov=FALSE; return TRUE;}
           SendCommand(idCommDev,1,lpMotorInfo->cName,'-',1,0) ;
           if( IsHomeYet(lpMotorInfo->cName, 'H'))
              {KillTimer(hDlg, TIMER_ID); lpMotorInfo->bMov=FALSE; return TRUE;}
           }
           }
        }
     else
        {
        if(!IsMotorMoving(lpMotorInfo->cName))
           {
           if ( ((lpMotorInfo->nDir==SW_A_DIR) && IsHomeYet(lpMotorInfo->cName, 'A')) ||
               ((lpMotorInfo->nDir==SW_B_DIR) && IsHomeYet(lpMotorInfo->cName, 'B')) ||
               IsHomeYet(lpMotorInfo->cName, 'H') )
             {KillTimer(hDlg, TIMER_ID) ; lpMotorInfo->bMov=FALSE; return TRUE ; }
           }
        }
     break ;
        }
     default:
        {KillTimer(hDlg, TIMER_ID) ; lpMotorInfo->bMov=FALSE; return TRUE ; }
     }
  if (lpMotorInfo->nTry > 60)
     {
     lpMotorInfo->bMov=FALSE;
     SendCommand(idCommDev, 0, lpMotorInfo->cName, cEscape, 0, 0) ;
     KillTimer(hDlg, TIMER_ID) ;
     wsprintf(szBuffer,"%c motor failed !", lpMotorInfo->cName) ;
```

```
      MessageBox(hDlg, szBuffer, "Motor ERROR", MB_OK|MB_ICONEXCLAMATION);
      return FALSE;
    }
}

BOOL FAR PASCAL _export
WaferDlg (HWND hDlg, UINT message,
             UINT wParam, LONG lParam)
{
  static int bDevLocked = 0 ; // 0: not locked !0:hWnd of lock Wnd
  static BOOL bLoaded;
  static BOOL bScriptRunning = FALSE ;
  static int bRefill = FALSE;
  static int nSameLevel = 10;
  static int nSameStepLimit = 10;
  static int WaitingForSYTimer=0;
  static int nTimerRetry;
  static DOUBLEPNT PtTmp, PtInit, PtEnd, PtCenter;
  static double Radius;
  static int nWaferSize;
  static VCA3KDATA VcaData[50] ;
  static int nIndex=0 ;
  static HANDLE hList=NULL ;
  static MOTORINFO XInfo, RInfo, SInfo, TInfo ;
  POLAR Disp;
  HDC hdc, hdcMem;
  PAINTSTRUCT ps;
  RECT rect;
  HBITMAP hOldBmp ;
  int i;
  double dTmp ;

switch (message)
    {
    case WM_INITDIALOG:
      {
        RECT RcMDIClient, RcDlg ;

SetCursor(LoadCursor(NULL, IDC_WAIT));
        GetWindowRect( hWndMDIClient, &RcMDIClient ) ;
        GetWindowRect( hDlg, &RcDlg ) ;
        SetWindowPos(hDlg, HWND_TOP,
                   RcMDIClient.right-(RcDlg.right-RcDlg.left), RcMDIClient.top,
                   RcDlg.right-RcDlg.left, RcDlg.bottom-RcDlg.top,SWP_NOSIZE) ;
        GetClientRect (hDlg, &rect);
        Radius = (double) (rect.bottom - 20) / 2;
        PtCenter.x = Radius + 10 ;  PtCenter.y = Radius + 10 ;
        PtEnd.x = 0.0 ; PtEnd.y = 0.0 ; PtInit = PtEnd ;
    nWaferSize = GetPrivateProfileInt("WINVCA","WaferSize", 125,"WINVCA.INI");
    nSyringeSpeed = GetPrivateProfileInt("WINVCA","Syringe_Speed",
                        0,"WINVCA.INI");
    nSyringeSize = GetPrivateProfileInt("WINVCA","Syringe_Type",
                        0,"WINVCA.INI");

dDropletSize = GetPrivateProfileDouble("WINVCA","DropletSize",
                           1.00, "WINVCA.INI");
        //initialize com port and setup motor drivers
        if (! InitMotors(hDlg) )
        {
          EnableItem( hDlg, IDOK, FALSE);
          EnableItem( hDlg, IDC_LOAD, FALSE);
          EnableItem( hDlg, IDC_SY_REFILL, FALSE);
          return FALSE ;
```

```
            }
          bLoaded = TRUE ;
              SendMessage(hDlg, WM_COMMAND, IDC_LOAD, 0L) ;
              SetCursor(LoadCursor(NULL, IDC_ARROW));
              return TRUE;
            } case IDC_CENTERWAFER:
        EnableItem( hDlg, IDOK, FALSE) ;
        EnableItem( hDlg, IDC_LOAD, FALSE) ;
        EnableItem( hDlg, IDC_SY_REFILL, FALSE) ;
        nIndex=0 ;         // reset & remove Markers
        PtEnd.x = 0.0 ; PtEnd.y = 0.0 ; PtInit = PtEnd; // Reset Initial Location
        InvalidateRect (hDlg, NULL, TRUE);
        if (! IsHomeYet(cTiltName,'A'))
      AddAction((HANDLE*)&hList, cTiltName, 2, cFindHome, DEF_T_FINDHOME, 0, FALSE) ;
        if (! IsHomeYet(cXName,'B'))
      AddAction(&hList, cXName, 2, cFindHome, DEF_X_FINDHOME, 1, FALSE) ;
          i = GetPrivateProfileInt("WINVCA","Sensor_Steps", DEF_SENSOR_STEPS,"WINVCA.INI");
          AddAction(&hList, cTiltName, 1, '-', i, 0, TRUE) ;
          AddAction(&hList, cRotateName,2, cFindHome, DEF_R_FINDHOME, 0, FALSE) ;
          AddAction(&hList, cRotateName, 1, '-', (int)(90/DEF_R_RATIO), 0, TRUE) ;
          AddAction(&hList, cTiltName, 1, '-', 175, 0, TRUE) ;
          AddAction(&hList, cXName, 2, cFindHome, DEF_X_SLEW, 0, TRUE ) ;
          AddAction(&hList, cXName, 1, 'A', 56, 0, TRUE ) ;
          AddAction(&hList, cXName, 1, '-', 100, 0, TRUE ) ;
          AddAction(&hList, cTiltName, 1, '+', 175, 0, TRUE) ;
          AddBtnCtrl( &hList, IDOK, TRUE) ;
          AddBtnCtrl( &hList, IDC_LOAD, TRUE) ;
          StartSequence( hDlg ) ;
          break ;

case WM_INIT_STAGE:
        {
        // unload
        EnableItem( hDlg, IDOK, FALSE) ;
        EnableItem( hDlg, IDC_LOAD, FALSE) ;
        EnableItem( hDlg, IDC_SY_REFILL, FALSE) ;
        nIndex=0 ;         // reset & remove Markers
        PtEnd.x = 0.0 ; PtEnd.y = 0.0 ; PtInit = PtEnd; // Reset Initial Location
        InvalidateRect (hDlg, NULL, TRUE);
        if (! IsHomeYet(cTiltName,'A'))
          AddAction((HANDLE*)&hList, cTiltName, 2, cFindHome, DEF_T_FINDHOME, 0, FALSE) ;
        if (! IsHomeYet(cXName,'B'))
          AddAction(&hList, cXName, 2, cFindHome, DEF_X_FINDHOME, 1, FALSE) ;
//        i = GetPrivateProfileInt("WINVCA","Sensor_Steps", 320,"WINVCA.INI");
//        AddAction(&hList, cTiltName, 1, '-', i, 0, TRUE) ;
//        i = GetPrivateProfileInt("WINVCA","StageOffset", 300,"WINVCA.INI");
//        AddAction(&hList, cXName, 1, '+', i, 0, TRUE) ;
//        AddAction(&hList, cRotateName, 2, cFindHome, 200, 0, FALSE) ;
//        AddAction(&hList, cTiltName, 2, cFindHome, 200, 0, TRUE) ;
//        AddAction(&hList, cXName, 2, cFindHome, 1000, 1, FALSE) ;
//        AddAction(&hList, cRotateName, 1, '-', (int)(90/.2877176), 0, FALSE) ;
        // load
        i = GetPrivateProfileInt("WINVCA","NeedleLength", DEF_NEEDLE_LEN,"WINVCA.INI");
        AddAction(&hList, cXName, 2, cFindHome, DEF_X_FINDHOME, 0, TRUE) ;
        AddAction(&hList, cTiltName, 1, '-', i, 0, TRUE) ;
        AddBtnCtrl( &hList, IDOK, TRUE) ;
        AddBtnCtrl( &hList, IDC_LOAD, TRUE) ;
        StartSequence( hDlg ) ;
        SetDlgItemText(hDlg, IDC_LOAD, (LPSTR) "&Unload");
        bLoaded = TRUE ;
        }
```

```
          break ;

case WM_SYSCOMMAND:
         switch (wParam)
       {
          case SC_CLOSE:
          ShowWindow(hDlg, SW_HIDE) ; return TRUE;
       }
         break;

case WM_CHK_LOCK:
         if(wParam==SET_LOCK)   // set lock
         bDevLocked = *((HWND*)lParam) ;
         if(wParam==READ_LOCK)
       *((HWND*)lParam) = bDevLocked ;
         return(TRUE) ;

case WM_SET_VARS:
         switch(wParam)
       {
       case IDC_SET_SY_SIZE:
         nSyringeSize = (int) lParam ;  break ;
       case IDC_SET_SY_SPEED:
         nSyringeSpeed = (int) lParam ;  break ;
       case IDC_SET_DROP_SIZE:
         dDropletSize = *((double*)lParam) ; break ;
       case IDC_SET_WAFER_SIZE:
         nWaferSize = (int) lParam ; break ;
       }
         InvalidateRect (hDlg, NULL, TRUE);
         return TRUE;

//     case WM_DRAWITEM:
//        hdc=GetWindowDC(GetDlgItem(hDlg, IDC_ZOOM));
//        hdcMem = CreateCompatibleDC (hdc);
//        hOldBmp = SelectObject (hdcMem, LoadBitmap (hInst, MAKEINTRESOURCE(IDB_ZOOM)));
//        BitBlt (hdc, 0, 0, 30, 30, hdcMem, 0, 0, SRCCOPY);
//        DeleteObject (SelectObject (hdcMem, hOldBmp));
//        DeleteDC (hdcMem);
//        return TRUE ;

case IDC_SETPNT:
         PtEnd =  *((DOUBLEPNT*)lParam) ;
         return TRUE ;

case IDC_SETSCRIPTINFO:
         if(wParam) bScriptRunning = TRUE ;
         else bScriptRunning = FALSE ;
         return TRUE ;

case IDC_GETSCRIPTINFO:
         if( bScriptRunning )  *((BOOL*) lParam) = TRUE ;
         else *((BOOL*) lParam) = FALSE ;
         return TRUE ;

case IDC_STAGEUNLOADED:
         if (! bLoaded) *(int*)lParam = TRUE ;
         else *(int*)lParam = FALSE ;
         return TRUE ;

case IDC_COMPLETEYET:
         if ( hList != NULL ) *((BOOL*)lParam) = FALSE ;
         else *((BOOL*)lParam) = TRUE ;
```

```
    return TRUE ;

case WM_PAINT:
  hdc = BeginPaint (hDlg, &ps);
  {
POINT ptCtr ;
ptCtr.x = (int) PtCenter.x ; ptCtr.y = (int) PtCenter.y ;
DrawGrid(hdc, ptCtr, (int)Radius, nWaferSize);
  }
  hdcMem = CreateCompatibleDC (hdc);
  hOldBmp = SelectObject (hdcMem, LoadBitmap (hInst, MAKEINTRESOURCE(IDB_LOCATOR)));
  PtTmp = DeNormalizePnt(PtEnd, PtCenter, Radius) ;
  BitBlt (hdc, (int) PtTmp.x - 9, (int) PtTmp.y - 9, 18, 18, hdcMem, 0, 0, SRCAND);
  DeleteObject (SelectObject (hdcMem, hOldBmp));

SelectObject( hdc, GetStockObject(ANSI_FIXED_FONT)) ;
  hOldBmp = SelectObject (hdcMem, LoadBitmap (hInst, MAKEINTRESOURCE(IDB_MARKER)));
  i = nIndex ;
  while (i)
    {
      PtTmp = DeNormalizePnt(VcaData[i].pt, PtCenter, Radius) ;
      BitBlt (hdc, (int) PtTmp.x-4, (int) PtTmp.y -4, 9, 9, hdcMem, 0, 0, SRCCOPY);
      if ( VcaData[i].angle == 999 )
        wsprintf( szBuffer, "XX" ) ;
      else
        wsprintf( szBuffer, "%d", VcaData[i].angle ) ;
      TextOut(hdc,(int)PtTmp.x+4,(int)PtTmp.y-4, szBuffer, strlen(szBuffer)) ;
      i-- ;
    }
  DeleteObject (SelectObject (hdcMem, hOldBmp));
  DeleteDC (hdcMem);
  EndPaint (hDlg, &ps);
  return TRUE;

case WM_LBUTTONDOWN:
  if (!(wParam & MK_SHIFT))
    {
      PtTmp.x = (double) LOWORD (lParam);
      PtTmp.y = (double) HIWORD (lParam);

if ( ((PtTmp.x-PtCenter.x)*(PtTmp.x-PtCenter.x)+
           (PtTmp.y-PtCenter.y)*(PtTmp.y-PtCenter.y))
          < (Radius-10)*(Radius-10))
        {
          PtEnd = NormalizePnt(PtTmp,PtCenter,Radius);
          InvalidateRect (hDlg, NULL, TRUE);
        }
      return 0;
    } case WM_TIMER:
  switch (wParam)
    {
    case ACTION_TIMER:
      {
        ACTION CurAct ;
        if( hList == NULL)
          { KillTimer(hDlg, ACTION_TIMER) ; return TRUE ; }
    PeekNextAction(&hList, &CurAct ) ;
    // wait for last action to complete
        if ((CurAct.Wait==TRUE) && (RInfo.bMov||SInfo.bMov||TInfo.bMov||XInfo.bMov))
          return FALSE ;
          GetNextAction(&hList, &CurAct ) ;
```

```c
            switch ( CurAct.ID )
              {
              case 'B': // set button status
                 EnableItem(hDlg, CurAct.Data1, CurAct.Data2) ;  break ;
              case 'M': // send AutoCal message
                 SendMessage(hWndFrame, CurAct.Data1, CurAct.Data2, 0L) ;
                 if ( CurAct.Command != NULL && nIndex < 49 )
                    {
                    nIndex++ ; VcaData[nIndex].pt=PtInit;
                    if (CalcData.bGood) VcaData[nIndex].angle=(int)CalcData.dLeftAngle ;
                    else VcaData[nIndex].angle= 999 ;    // Bad data
                    InvalidateRect (hDlg, NULL, TRUE);
                    }
                 break ;
              case 'R':
         StartMotor(hDlg, (LPMOTORINFO) &RInfo, CHK_R_TIMER, CurAct);
                 break ;
              case 'S':
         StartMotor(hDlg, (LPMOTORINFO) &SInfo, CHK_S_TIMER, CurAct);
                 break ;
              case 'T':
         StartMotor(hDlg, (LPMOTORINFO) &TInfo, CHK_T_TIMER, CurAct);
                 break ;
              case 'X':
         StartMotor(hDlg, (LPMOTORINFO) &XInfo, CHK_X_TIMER, CurAct);
         break;
              }
            return TRUE;
         }
       case CHK_R_TIMER:
      return(CheckMotorStatus(hDlg, (LPMOTORINFO) &RInfo, CHK_R_TIMER));
       case CHK_S_TIMER:
      return(CheckMotorStatus(hDlg, (LPMOTORINFO) &SInfo, CHK_S_TIMER));
       case CHK_T_TIMER:
      return(CheckMotorStatus(hDlg, (LPMOTORINFO) &TInfo, CHK_T_TIMER));
       case CHK_X_TIMER:
      return(CheckMotorStatus(hDlg, (LPMOTORINFO) &XInfo, CHK_X_TIMER));
   }
   return FALSE ;

case WM_COMMAND:
       switch (wParam)
          {
          case IDC_LOAD:    // toggle load and unload
       if ( !bLoaded )
             {                        // do load
              EnableItem( hDlg, IDOK, FALSE) ;
              EnableItem( hDlg, IDC_LOAD, FALSE) ;
              EnableItem( hDlg, IDC_SY_REFILL, FALSE) ;
              i = GetPrivateProfileInt("WINVCA","NeedleLength", DEF_NEEDLE_LEN,"WINVCA.INI")
;
       AddAction(&hList, cXName, 1, 'A', 56, 0, FALSE) ; // turn on Valve and LED
              AddAction(&hList, cXName, 2, cFindHome, DEF_X_FINDHOME, 0, FALSE) ;
              AddAction(&hList, cTiltName, 1, '-', i, 0, TRUE) ;
              AddBtnCtrl( &hList, IDOK, TRUE) ;
              AddBtnCtrl( &hList, IDC_LOAD, TRUE) ;
              StartSequence( hDlg ) ;
              SetDlgItemText(hDlg, IDC_LOAD, (LPSTR) "&Unload");
              bLoaded = TRUE ;
              PtEnd.x = 0.0 ; PtEnd.y = 0.0 ; PtInit = PtEnd; // Reset Initial Location
              InvalidateRect (hDlg, NULL, TRUE);
              return TRUE ;
             }
```

```
              else
                {                        // do unload
                  EnableItem( hDlg, IDOK, FALSE) ;
                  EnableItem( hDlg, IDC_LOAD, FALSE) ;
                  EnableItem( hDlg, IDC_SY_REFILL, FALSE) ;
                  nIndex=0 ;         // reset & remove Markers
                  PtEnd.x = 0.0 ; PtEnd.y = 0.0 ; PtInit = PtEnd; // Reset Initial Location
                  InvalidateRect (hDlg, NULL, TRUE);
                  if (! IsHomeYet(cTiltName,'A'))
                     AddAction((HANDLE*)&hList, cTiltName, 2, cFindHome, DEF_T_FINDHOME, 0, FALSE
) ;
                  if (! IsHomeYet(cXName,'B'))
                     AddAction(&hList, cXName, 2, cFindHome, DEF_X_FINDHOME, 1, FALSE) ;
          i = GetPrivateProfileInt("WINVCA","Sensor_Steps", DEF_SENSOR_STEPS,"WINVCA.INI");
          AddAction(&hList, cTiltName, 1, '-', i, 0, TRUE) ;
          AddAction(&hList, cRotateName,2, cFindHome, DEF_R_FINDHOME, 0, FALSE) ;
          AddAction(&hList, cTiltName, 2, cFindHome, DEF_T_FINDHOME, 0, TRUE) ;
          AddAction(&hList, cXName, 1, 'A', 0, 0, FALSE) ;  // turn off Valve and LED
                  AddBtnCtrl( &hList, IDC_LOAD, TRUE) ;
                  AddBtnCtrl( &hList, IDC_SY_REFILL, TRUE) ;
                  StartSequence( hDlg ) ;
                  SetDlgItemText(hDlg, IDC_LOAD, (LPSTR) "&Load");
                  bLoaded = FALSE ;
                  return TRUE ;
                } case IDC_SY_REFILL:
       SetCursor(LoadCursor(NULL, IDC_WAIT));
       hList=1 ;  // not null->make other WNDs know SY is moving *****
       bRefill=SynchroFindLimit(cSyringeName, 'A', DEF_S_FINDHOME) ;
       SendCommand(idCommDev,0,cSyringeName,cSetOrigin,0,0);
       dSyringeSteps = 0.0;
       SetDlgItemText(hDlg, IDC_SY_LEVEL, (LPSTR)"100.0");
       hList = NULL ; // done refill ********************
       SetCursor(LoadCursor(NULL, IDC_ARROW));
       return TRUE;

case IDOK:
           EnableItem( hDlg, IDOK, FALSE);
           EnableItem( hDlg, IDC_LOAD, FALSE);
           Disp = GetDisplacement (PtInit, PtEnd);
           PtInit = PtEnd;

dTmp = GetPrivateProfileDouble("WINVCA","R_Ratio",
                     DEF_R_RATIO, "WINVCA.INI");
           i = (int) (fabs(Disp.theta)/dTmp) ;
           if ( Disp.theta > 0 )
             AddAction(&hList, cRotateName, 1, '-',i , 0, FALSE) ;
           else if ( Disp.theta < 0 )
             AddAction(&hList, cRotateName, 1, '+',i , 0, FALSE) ;
           dTmp = GetPrivateProfileDouble("WINVCA","X_Ratio", DEF_X_RATIO, "WINVCA.INI");
           i=(int) ((fabs(Disp.r)*((nWaferSize/25.4)/2))/dTmp);
           if ( Disp.r > 0 )
             AddAction(&hList, cXName, 1, '-',i , 0, FALSE) ;
           else if ( Disp.r < 0 )
             AddAction(&hList, cXName, 1, '+',i , 0, FALSE) ;
           AddAction(&hList, cTiltName, 1,'-',100 , 0, TRUE) ;
           i = (int)(dDropletSize / (dVolumePerStep * dFactor[nSyringeSize]));
           AddAction(&hList, cSyringeName, 1, '-', i, 0, FALSE) ;
           AddAction(&hList, cTiltName, 1, '+', 100, 0, TRUE) ;
       if ( !bScriptRunning )
{
     AddMsgCtrl(&hList,  WM_COMMAND, IDM_CAPIMAGE,TRUE, NULL) ;
```

```
            AddMsgCtrl(&hList,  WM_COMMAND, IDM_AUTO_CALC, FALSE, !NULL) ;
            AddBtnCtrl( &hList, IDOK, TRUE);
        }
                AddBtnCtrl( &hList, IDC_LOAD, TRUE);
                StartSequence( hDlg ) ;
                return TRUE;

case IDCANCEL:
                ShowWindow (hDlg, SW_HIDE);
                return TRUE;
            }
            break;
    }
    return FALSE;
}

BOOL FAR PASCAL _export
WaferSetupDlg (HWND hDlg, UINT message,
                UINT wParam, LONG lParam)
{
    static int nWaferSize;
    static char* szWaferSize[5] = {" 75 m.m.", "100 m.m.",
                    "125 m.m.", "150 m.m.", "200 m.m."} ;
    LPSTR ptr ;
    int i ;

switch (message)
        {
        case WM_INITDIALOG:
            {
            // initialize and insert combo box values
            // wafer size
            for ( i = 0; i < 5; i++ )
                SendMessage(GetDlgItem (hDlg, IDC_WSIZE),
                        CB_ADDSTRING, 0, (LONG) szWaferSize[i]);
            nWaferSize = GetPrivateProfileInt("WINVCA","WaferSize", DEF_WAFER_SIZE, "WINVCA.INI");
        if(nWaferSize<200) i= (nWaferSize/25)-3 ; else i= (nWaferSize/25)-4 ;
            SendMessage(GetDlgItem (hDlg, IDC_WSIZE), CB_SETCURSEL, i, 0L);
            // syringe speed
            ptr = (LPSTR) szSpeed;
            for ( i = 0; i < 3; ++i, ptr+=7)
                SendMessage(GetDlgItem (hDlg, IDC_SY_SPEED), CB_ADDSTRING, 0, (LONG) ptr);
            nSyringeSpeed = GetPrivateProfileInt("WINVCA","Syringe_Speed",
                                        0,"WINVCA.INI");
            SendMessage(GetDlgItem (hDlg, IDC_SY_SPEED),
                        CB_SETCURSEL, nSyringeSpeed, 0L);
            // syringe size
            ptr = (LPSTR) szSYType;
            for ( i = 0; i < 3; ++i, ptr+=7)
                SendMessage(GetDlgItem (hDlg, IDC_SY_SIZE),
                        CB_ADDSTRING, 0, (LONG) ptr);
            nSyringeSize = GetPrivateProfileInt("WINVCA","Syringe_Type",
                                        0,"WINVCA.INI");
            SendMessage(GetDlgItem (hDlg, IDC_SY_SIZE),
                        CB_SETCURSEL, nSyringeSize, 0L);
            // droplet size
        dDropletSize = GetPrivateProfileDouble("WINVCA","DropletSize",
                            1.00, "WINVCA.INI");
            sprintf(szBuffer, "%5.1f", dDropletSize);
            SetDlgItemText(hDlg, IDC_SY_DROPLET, (LPSTR) szBuffer);
            return TRUE;
        }
```

```
case WM_COMMAND:
  switch (wParam)
    {
    case IDC_WSIZE :
      if (HIWORD(lParam) == CBN_SELCHANGE)
        {
           i = (int) SendMessage(GetDlgItem(hDlg, IDC_WSIZE), CB_GETCURSEL, 0, OL);
           if(i<4) nWaferSize = (i+3)*25 ; else nWaferSize = (i+4)*25 ;
        return TRUE ;
        }
           break ;

case IDC_SY_DROPLET:
      if (HIWORD(lParam)==EN_KILLFOCUS)
        {
           int i = GetDlgItemText(hDlg,wParam,(LPSTR) szBuffer,
                             SIZEOFBUFFER);
           szBuffer[i] = '\0';
           if (IsDigitString((LPSTR) szBuffer, TRUE))
              dDropletSize = atof(szBuffer);
           else dDropletSize = 1.0;
           sprintf(szBuffer, "%5.1f", dDropletSize);
           SetDlgItemText(hDlg, IDC_SY_DROPLET, (LPSTR) szBuffer);
           return TRUE;
        }
      break;

case IDC_SY_SPEED:
      if (HIWORD(lParam) == CBN_SELCHANGE)
        {
           int New = (int) SendMessage(GetDlgItem(hDlg, IDC_SY_SPEED), CB_GETCURSEL, 0, OL);
           if (nSyringeSpeed != New)
              SendCommand(idCommDev,1,cSyringeName,cSlewRate,
                        SyringeSpeed[New],0);
           nSyringeSpeed = New;
           return TRUE;
        }
      break;

case IDC_SY_SIZE:
      if (HIWORD(lParam) == CBN_SELCHANGE)
        {
           nSyringeSize
              = (WORD) SendMessage(GetDlgItem(hDlg, IDC_SY_SIZE),
                             CB_GETCURSEL, 0, OL);
           return TRUE;
        }
      break;

case IDOK:
      wsprintf(szBuffer,"%d", nWaferSize) ;
      WritePrivateProfileString("WINVCA", "WaferSize", szBuffer, "WINVCA.INI");
    SendMessage(hWndLocator, WM_SET_VARS, IDC_SET_WAFER_SIZE, (long) nWaferSize) ;
      sprintf(szBuffer, "%5.1f", dDropletSize);
      WritePrivateProfileString("WINVCA", "DropletSize", szBuffer, "WINVCA.INI");
    SendMessage(hWndLocator, WM_SET_VARS, IDC_SET_DROP_SIZE, (LPARAM) &dDropletSize);
      wsprintf((LPSTR)szBuffer, "%d",nSyringeSpeed);
      WritePrivateProfileString("WINVCA", "Syringe_Speed",
                           (LPSTR) szBuffer, "WINVCA.INI");
    SendMessage(hWndLocator, WM_SET_VARS, IDC_SET_SY_SPEED, (long) nSyringeSpeed);
      wsprintf((LPSTR)szBuffer, "%d", nSyringeSize);
      WritePrivateProfileString("WINVCA", "Syringe_Type",
                           (LPSTR) szBuffer, "WINVCA.INI");
```

```
      SendMessage(hWndLocator, WM_SET_VARS, IDC_SET_SY_SIZE, (long) nSyringeSize) ;
         EndDialog(hDlg, 0) ;
         return TRUE;

case IDCANCEL:
       EndDialog(hDlg, 0) ;
         return TRUE;
        }
    break;
    }
  return FALSE;
}

BOOL FAR PASCAL _export
ScriptRunnerDlg (HWND hDlg, UINT message,
              UINT wParam, LONG lParam)
{
  static DOUBLEPNT PtEnd, PtCenter ;
  static DOUBLEPNT TestPnt[50] ;
  DOUBLEPNT PtTmp;
  int nWaferSize ;
  static double Radius;
  HRGN hRgnWafer, hRgnClip;
  static int nIndex=0 ;
  static BOOL Recording = FALSE ;
  HDC hdc, hdcMem;
  PAINTSTRUCT ps;
  RECT rect;
  int i ;
  HBITMAP hOldBmp ;

switch (message)
     {
     case WM_INITDIALOG:
       {
         CenterDialog( hDlg ) ;
         nWaferSize = GetPrivateProfileInt("WINVCA","WaferSize", DEF_WAFER_SIZE,"WINVCA.INI");
         EnableItem( hDlg, IDC_RUN, FALSE);
         GetClientRect (hDlg, &rect);
         Radius = (double) (rect.bottom - 20) / 2;
         PtCenter.x = Radius + 10 ;  PtCenter.y = Radius + 10 ;
         PtEnd.x = 0.0 ; PtEnd.y = 0.0 ;
         return TRUE ;
       } case WM_ACTIVATE:
       if ( hWndLocator )  ShowWindow(hWndLocator, SW_HIDE) ;
       return FALSE;

case WM_SYSCOMMAND:
       switch (wParam)
     {
     case SC_CLOSE:
       ShowWindow(hDlg, SW_HIDE) ;   return FALSE;
     }
       break;

case WM_LBUTTONDOWN:

if (!(wParam & MK_SHIFT))
          {
            PtTmp.x = (double) LOWORD (lParam);         22
```

```
        PtTmp.y = (double) HIWORD (lParam);

if ( ((PtTmp.x-PtCenter.x)*(PtTmp.x-PtCenter.x)+
           (PtTmp.y-PtCenter.y)*(PtTmp.y-PtCenter.y))
          < (Radius-10)*(Radius-10))
        {
          PtEnd = NormalizePnt(PtTmp,PtCenter,Radius);
          if ( Recording && nIndex < 49 )
            {
              nIndex++ ;
              TestPnt[nIndex].x=  PtEnd.x ; TestPnt[nIndex].y=  PtEnd.y ;
            }
          InvalidateRect (hDlg, NULL, TRUE);
        }
      return 0;
    } case WM_PAINT:
  hdc = BeginPaint (hDlg, &ps);
  {
POINT ptCtr ;
ptCtr.x = (int) PtCenter.x ; ptCtr.y = (int) PtCenter.y ;
DrawGrid(hdc, ptCtr, (int)Radius, nWaferSize);
  }
  hdcMem = CreateCompatibleDC (hdc);
  hOldBmp = SelectObject (hdcMem, LoadBitmap (hInst, MAKEINTRESOURCE(IDB_LOCATOR)));
  PtTmp = DeNormalizePnt(PtEnd, PtCenter, Radius) ;
  BitBlt (hdc, (int) PtTmp.x - 9, (int) PtTmp.y - 9, 18, 18, hdcMem, 0, 0, SRCAND);
  DeleteObject (SelectObject (hdcMem, hOldBmp));

hOldBmp = SelectObject (hdcMem, LoadBitmap (hInst, MAKEINTRESOURCE(IDB_MARKER)));
  i = nIndex ;
  while (i)
     {
       PtTmp = DeNormalizePnt(TestPnt[i], PtCenter, Radius) ;
       BitBlt (hdc, (int) PtTmp.x-4, (int) PtTmp.y -4, 9, 9, hdcMem, 0, 0, SRCCOPY);
       i-- ;
     }
  DeleteObject (SelectObject (hdcMem, hOldBmp));
  DeleteDC (hdcMem);
  DeleteObject (hRgnClip);
  DeleteObject (hRgnWafer);
  EndPaint (hDlg, &ps);
  return TRUE;

case WM_TIMER:
  switch(wParam)
     {
     case SCRIPT_TIMER:
  {
    BOOL bJobDone = NULL;
    SendMessage(hWndLocator, IDC_COMPLETEYET,0, (LPARAM) &bJobDone) ;
    if ( nIndex ==0 && bJobDone)
       {
    KillTimer(hDlg, SCRIPT_TIMER) ;
    MessageBox(hDlg, "Script Completed! Press \"OK\" to unload the wafer.",
           "Script Runner", MB_OK) ;
    DestroyWindow(hWndScriptRunner) ;
    hWndScriptRunner = NULL ;
    SendMessage( hWndLocator, WM_COMMAND, IDC_LOAD,0 ) ;
    return TRUE ;
       }
    if ( bJobDone )
```

```
            {
        SendMessage( hWndLocator, IDC_SETPNT, 0,(LPARAM) &TestPnt[nIndex] ) ;
        SendMessage( hWndLocator, WM_COMMAND, IDOK, 0L) ;
        nIndex -- ;
        return TRUE ;
            }
        break ;
      }
        }
      return FALSE ;

case WM_COMMAND:
       switch (wParam)
          {
          case IDC_RUN:
             {
              if(nIndex)
                 {
                  if(! IsHomeYet(cXName,'B') )
                     {
                       MessageBox(hDlg, "Please unload the stage before you run the script",
                                  "Warrning", MB_OK);
                       ShowWindow(hWndLocator, SW_SHOW) ;
                       return TRUE ;
                     }
                  SendMessage( hWndLocator, WM_COMMAND,IDC_LOAD ,0 ) ;
                  ShowWindow(hWndLocator, SW_SHOW) ;
                  ShowWindow(hWndScriptRunner, SW_HIDE) ;
                  EnableItem( hDlg, IDC_RUN, FALSE);
                  SetTimer(hDlg, SCRIPT_TIMER, 1000, NULL) ;
                 }
               break ;
             }
          case IDC_RECSCRIPT:
       if ( Recording == FALSE )
          {
           Recording = TRUE ;
           EnableItem( hDlg, IDC_RUN, FALSE);
           SetDlgItemText( hDlg, IDC_RECSCRIPT, "&Stop") ;
           return TRUE ;
          }
       if ( Recording == TRUE )
          {
           Recording = FALSE ;
           EnableItem( hDlg, IDC_RUN, TRUE);
           SetDlgItemText( hDlg, IDC_RECSCRIPT, "&Rec") ;
           return TRUE ;
          }
            break ;
          case IDC_CLOSE:
            ShowWindow(hDlg, SW_HIDE) ;
            return FALSE;
          }
       }
   return FALSE;
}

BOOL FAR PASCAL _export
ExerciserDlg (HWND hDlg, UINT message,
              UINT wParam, LONG lParam)
{                                              24
```

```
static int nTestPnt, nTestPntCount, nRepeat ;
static int stage=1 ;    // goingtoload=2 goingtounload=1
DOUBLEPNT dPnt ;

switch (message)
   {
   case WM_INITDIALOG:
      {
         CenterDialog( hDlg ) ;
      nTestPnt=nTestPntCount=3 ; nRepeat=3 ;
      SendMessage(GetDlgItem(hDlg, IDC_TESTPNT), WM_SETTEXT, 0, (LPARAM)((LPSTR)"10"));
      SendMessage(GetDlgItem(hDlg, IDC_REPEAT), WM_SETTEXT, 0, (LPARAM)((LPSTR)"10"));
      srand((unsigned) time(NULL));
      return TRUE ;
      } case WM_TIMER:
      switch(wParam)
         {
      case INIT_TIMER:
        {
          BOOL bJobDone;
          SendMessage(hWndLocator, IDC_COMPLETEYET,0, (LPARAM) &bJobDone) ;
          if ( bJobDone==TRUE && (stage==1 || stage==2) )
             {
             if (stage==1 && !IsHomeYet(cXName,'B') )   // do nothing if unload already ..
                SendMessage( hWndLocator, WM_COMMAND,IDC_LOAD ,0 ) ;
             if (stage==2 )    // load
                SendMessage( hWndLocator, WM_COMMAND,IDC_LOAD ,0 ) ;
             stage++ ;
             return TRUE ;
             }
          if (bJobDone==TRUE && (stage!=1 || stage!=2))
             {
             stage=1 ;   // reset to "goingtounload"
             KillTimer(hDlg, INIT_TIMER) ;
             SetTimer(hDlg, SCRIPT_TIMER, 1500, NULL) ;
             return TRUE ;
             }
          return FALSE ;
        } case SCRIPT_TIMER:
        {
          BOOL bJobDone = FALSE;

SendMessage(hWndLocator, IDC_COMPLETEYET,0, (LPARAM) &bJobDone) ;
          if ( nRepeat==0 && nTestPntCount==0 && bJobDone)
             {
             KillTimer(hDlg, SCRIPT_TIMER) ;
             EnableItem( hDlg, IDOK, TRUE);
             SendDlgItemMessage(hDlg, IDC_TESTPNT, EM_SETREADONLY, FALSE, 0L);
             SendDlgItemMessage(hDlg, IDC_REPEAT, EM_SETREADONLY, FALSE, 0L);
             MessageBox(hDlg, "Exercise Completed!" , "Exerciser", MB_OK) ;
             return TRUE ;
             }
          if ( bJobDone )
             {
             if ( nTestPntCount != 0 )
                {
                   double r, theta ;
                   r = ((double)rand()/(double)RAND_MAX) ;
                   theta = ((double)rand()/(double)RAND_MAX)*3.1415926*2.0 ;
```

```
                    dPnt.x= cos( theta )*r;
                    dPnt.y= sin( theta )*r;
                    SendMessage( hWndLocator, IDC_SETPNT, 0,(LPARAM) &dPnt) ;
                    SendMessage( hWndLocator, WM_COMMAND, IDOK, 0L) ;
                    nTestPntCount -- ;
                    wsprintf(szBuffer, "%d", nTestPntCount) ;
                    SendMessage(GetDlgItem(hDlg, IDC_TESTPNT), WM_SETTEXT, 0,
                        (LPARAM)((LPSTR)szBuffer));
                    wsprintf(szBuffer, "%d", nRepeat) ;
                    SendMessage(GetDlgItem(hDlg, IDC_REPEAT), WM_SETTEXT, 0,
                        (LPARAM)((LPSTR)szBuffer));
                }
                else if ( nTestPntCount == 0 && nRepeat != 0 )
                {
                    SendMessage( hWndLocator, WM_COMMAND,IDC_SY_REFILL,0 ) ;
                    SendMessage( hWndFrame, WM_COMMAND, IDM_CLOSEALL, 2L);
                    nTestPntCount = nTestPnt ;
                    nRepeat -- ;
                    KillTimer(hDlg, SCRIPT_TIMER) ;
                    SetTimer(hDlg, INIT_TIMER, 1500, NULL) ;
                }
                return TRUE ;
            }
            return FALSE ;
        }
        break ;
    }
        break ;

case WM_COMMAND:
    {
        switch (wParam)
        {
        case IDOK:
            {
                EnableItem( hDlg, IDOK, FALSE);
                SendDlgItemMessage(hDlg, IDC_TESTPNT, EM_SETREADONLY, TRUE, 0L);
                SendMessage(GetDlgItem(hDlg, IDC_TESTPNT), WM_GETTEXT,
                    SIZEOFBUFFER, (LPARAM) ((LPSTR) szBuffer));
                szBuffer[strlen(szBuffer)]='\0';
                nTestPnt = nTestPntCount = atoi(szBuffer) ;
                SendDlgItemMessage(hDlg, IDC_REPEAT, EM_SETREADONLY, TRUE, 0L);
                SendMessage(GetDlgItem(hDlg, IDC_REPEAT), WM_GETTEXT,
                    SIZEOFBUFFER, (LPARAM) ((LPSTR) szBuffer));
                szBuffer[strlen(szBuffer)]='\0';
                nRepeat = atoi(szBuffer)-1 ;
                SetTimer(hDlg, INIT_TIMER, 1500, NULL) ;
                return TRUE ;
            } case IDCANCEL:
            EndDialog(hDlg, 0) ;
            return TRUE;
        }
        }
    }
    return FALSE;
}
```

What is claimed is:

1. A system for positioning a substrate having a surface required to be characterized with a contact angle measurement, the system comprising:

a stage which supports the substrate;

a dispenser assembly having a dispensing tip through which a liquid droplet having a preselected volume is dispensed onto the surface of the substrate;

a first stepping motor mechanically coupled to the stage with a lead screw to move the stage in a horizontal direction;

a second stepping motor mechanically coupled to the stage with a belt and capstan mechanism to rotate the stage;

a third stepping motor mechanically coupled to the stage to change the vertical spacing between the dispensing tip and the surface of the substrate;

a fourth stepping motor mechanically coupled to the dispenser assembly to dispense the liquid droplet from the dispenser assembly; and a controller which delivers actuation signals to the first, second, third, and fourth stepping motors, so as to place the liquid droplet at a predetermined location on the surface of the substrate for performing the contact angle measurement.

2. The system of claim 1 wherein the dispenser assembly includes a syringe for carrying liquid, the syringe having a first end connected to the dispensing tip and a second end having a plunger connected to the fourth actuator.

3. The system of claim 2 wherein the stage include stop members which contact an edge of the substrate and the dispenser assembly includes a paddle member which is used to move the substrate into contact with the stop members, so that the substrate is substantially centered on the stage.

4. The system of claim 3 wherein the first actuating mechanism includes a lead screw which connects the first actuator to the stage.

5. The system of claim 4 wherein the first actuating mechanism includes a belt and capstan mechanism to connect the second actuator to the wafer stage.

* * * * *